(12) United States Patent
Langer et al.

(10) Patent No.: US 11,612,731 B2
(45) Date of Patent: Mar. 28, 2023

(54) FLUID HANDLING DEVICES

(71) Applicant: Colder Products Company, St. Paul, MN (US)

(72) Inventors: Elizabeth J. Langer, Minneapolis, MN (US); Randall S. Williams, Minneapolis, MN (US); Gary J. Harris, Maple Grove, MN (US)

(73) Assignee: Colder Products Company, Roseville, MN (US)

( * ) Notice: Subject to any disclaimer, the term of this patent is extended or adjusted under 35 U.S.C. 154(b) by 383 days.

(21) Appl. No.: 16/645,074

(22) PCT Filed: Sep. 28, 2018

(86) PCT No.: PCT/US2018/053410
§ 371 (c)(1),
(2) Date: Mar. 6, 2020

(87) PCT Pub. No.: WO2019/167891
PCT Pub. Date: Apr. 4, 2019

(65) Prior Publication Data
US 2020/0282197 A1    Sep. 10, 2020

Related U.S. Application Data

(60) Provisional application No. 62/659,473, filed on Apr. 18, 2018, provisional application No. 62/564,726, filed on Sep. 28, 2017.

(51) Int. Cl.
*A61M 39/10*     (2006.01)
*A61F 5/44*      (2006.01)

(52) U.S. Cl.
CPC ....... *A61M 39/1055* (2013.01); *A61F 5/4405* (2013.01); *A61M 39/1011* (2013.01);
(Continued)

(58) Field of Classification Search
CPC .. A61M 39/10; A61M 39/1055; A61M 39/16; A61M 39/22; A61M 39/26;
(Continued)

(56) References Cited

U.S. PATENT DOCUMENTS 2,397,576 A * 4/1946 Townhill .................. F16L 37/12
                                                137/599.02
3,943,962 A   3/1976 Nagy
(Continued)

FOREIGN PATENT DOCUMENTS

| CN | 104203333 | 4/2006 |
|----|-----------|--------|
| CN | 101242800 | 2/2012 |

(Continued)

OTHER PUBLICATIONS

Extended European Search Report in Application No. 18860563.8 dated Sep. 30, 2020, 7 pages.
(Continued)

*Primary Examiner* — Kami A Bosworth
(74) *Attorney, Agent, or Firm* — Fish & Richardson P.C.

(57) ABSTRACT

Quick disconnect fluid coupling devices described herein. The fluid couplings are configured for use in fluid systems for the purpose of providing a low-spill quick disconnect coupling. The fluid couplings include portions that are pivotable in relation to each other to open and close a fluid pathway through the fluid couplings. Particular embodiments of these fluid coupling can be configured to improve medical fluid handling equipment because the fluid coupling devices can be connected and disconnected (e.g., multiple times) while minimizing fluid spillage.

20 Claims, 19 Drawing Sheets

(52) U.S. Cl.
CPC ............... *A61M 2039/1005* (2013.01); *A61M 2039/1027* (2013.01)

(58) Field of Classification Search
CPC .. A61M 2039/1016; A61M 2039/1027; A61M 2039/262; A61M 2039/268; A61F 5/4405; F16K 5/0221; F16K 5/0228; F16K 5/0292; F16K 5/0421; F16K 5/0428; F16K 5/0492; F16K 5/0621; F16K 5/0626; F16K 11/12; F16L 37/373; F16L 37/47
See application file for complete search history.

(56) References Cited

U.S. PATENT DOCUMENTS

| | | |
|---|---|---|
| 5,492,147 A | 2/1996 | Challender |
| 9,611,965 B2 | 4/2017 | Cheon |
| 2005/0087241 A1* | 4/2005 | Kohda ................... F16L 37/23 137/614.03 |
| 2007/0007479 A1 | 1/2007 | Efinger et al. |
| 2008/0163941 A1 | 7/2008 | Lundman |
| 2015/0126958 A1* | 5/2015 | Sanders .................. A61J 1/201 285/330 |
| 2015/0314093 A1 | 11/2015 | Chiu |
| 2016/0022538 A1 | 1/2016 | Pavlik |
| 2019/0275316 A1* | 9/2019 | Stjernberg Bejhed .. F16L 37/28 |

FOREIGN PATENT DOCUMENTS

| | | |
|---|---|---|
| CN | 105042240 | 12/2014 |
| DE | 102014216971 | 3/2016 |
| EP | 1759136 | 3/2007 |
| WO | WO 2009050173 | 4/2009 |

OTHER PUBLICATIONS

International Preliminary Report on Patentability in PCT Appln. No. PCT/US2018/053410, dated Mar. 31, 2020, 9 pages.
International Search Report and Written Opinion in PCT Appln. No. PCT/US2018/053410, dated Dec. 12, 2018, 9 pages.

* cited by examiner

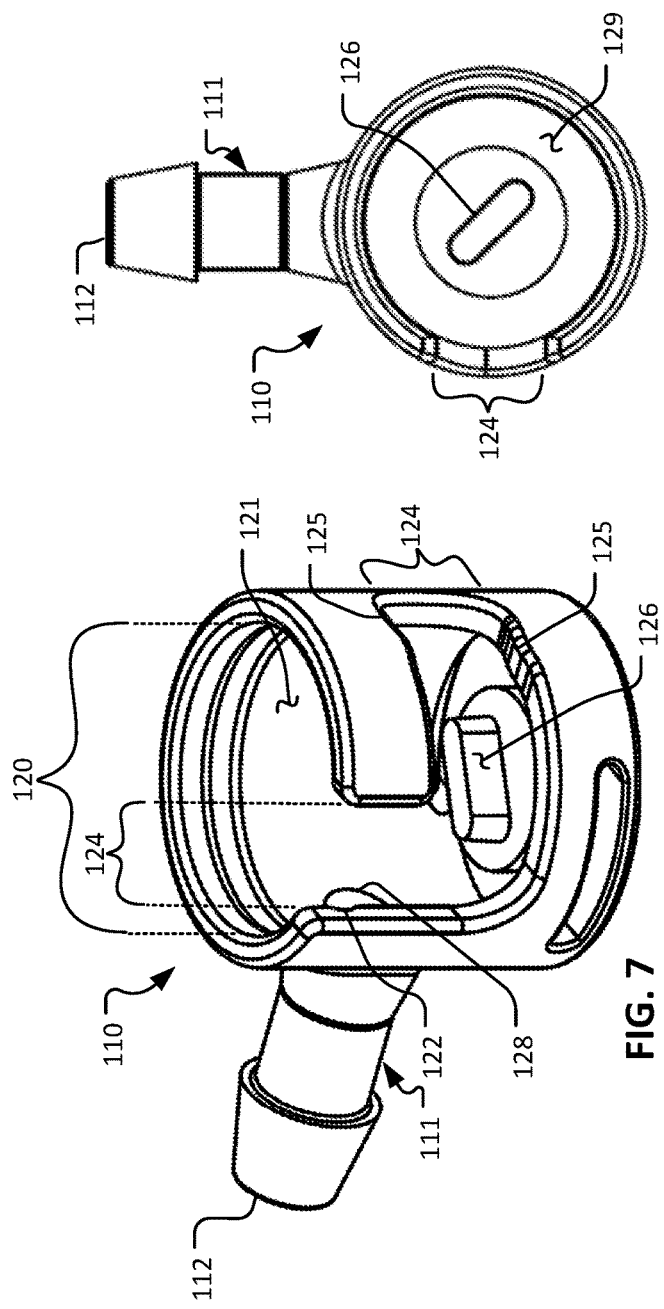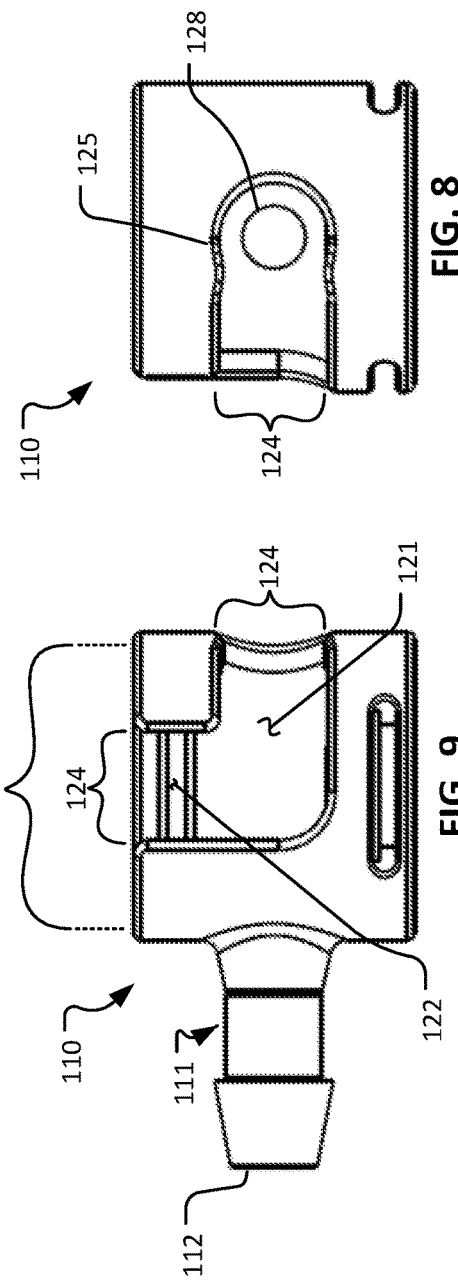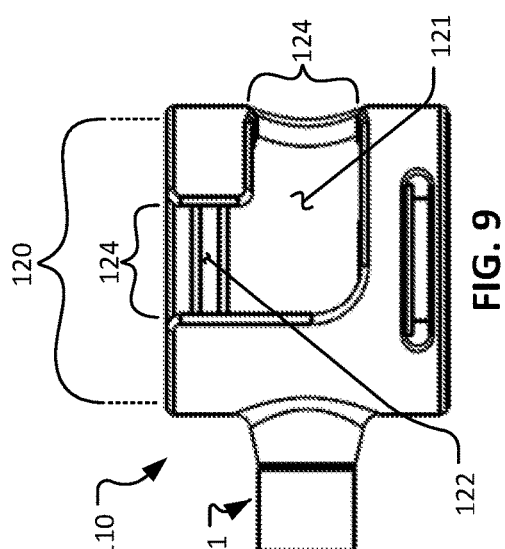

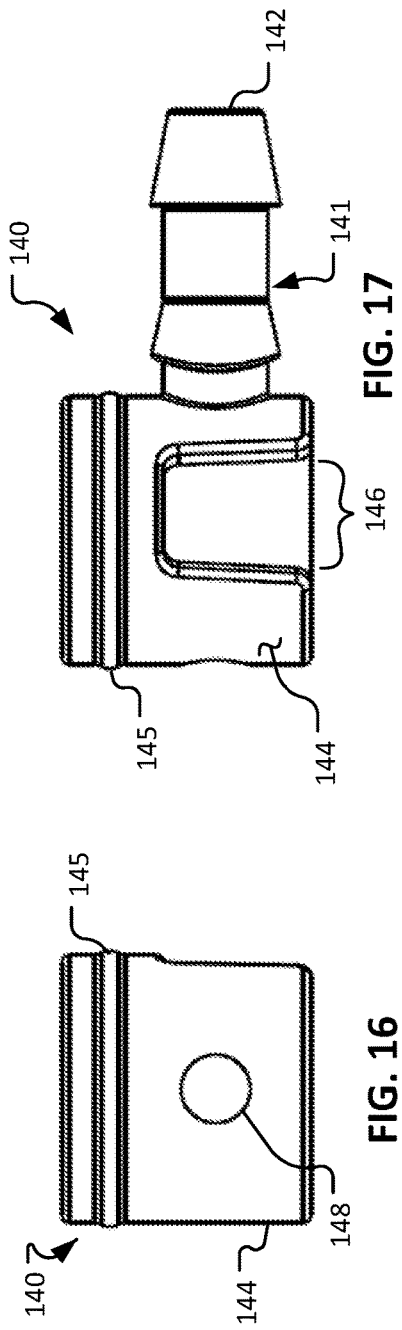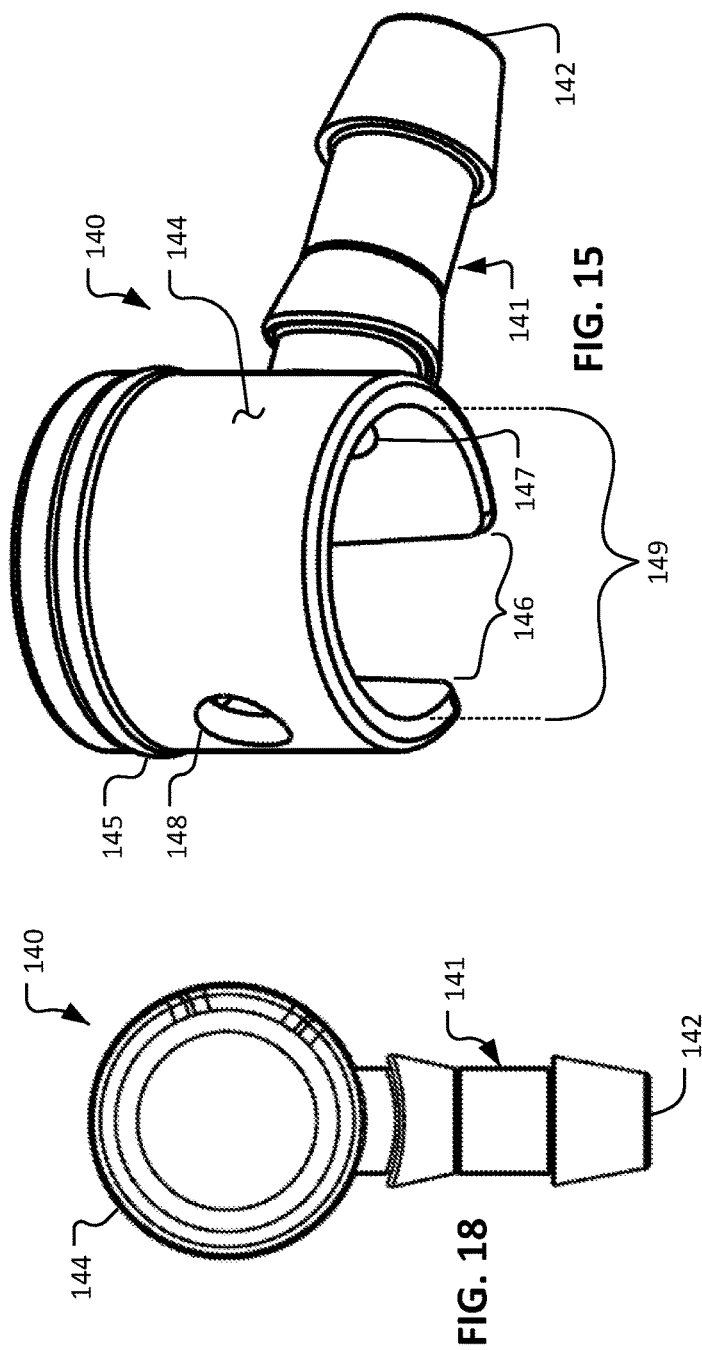

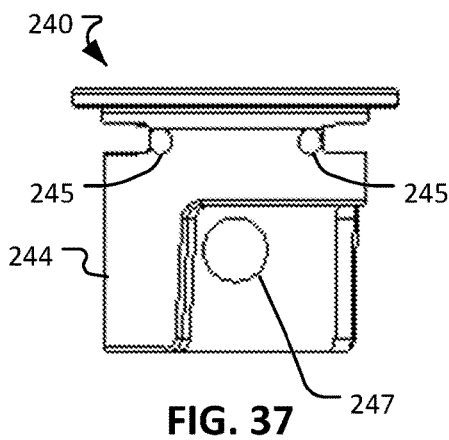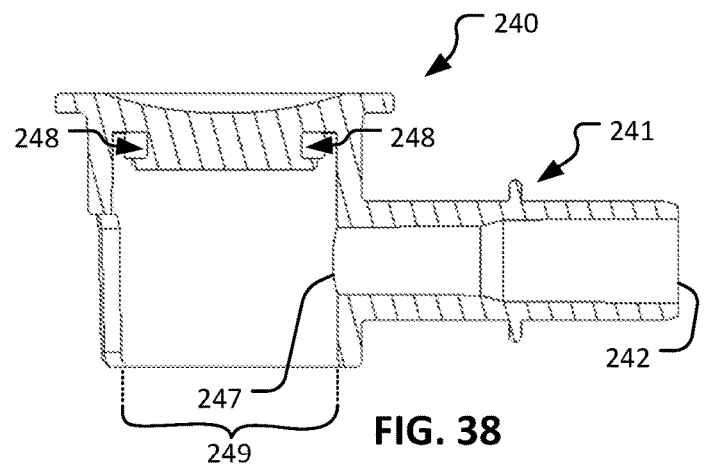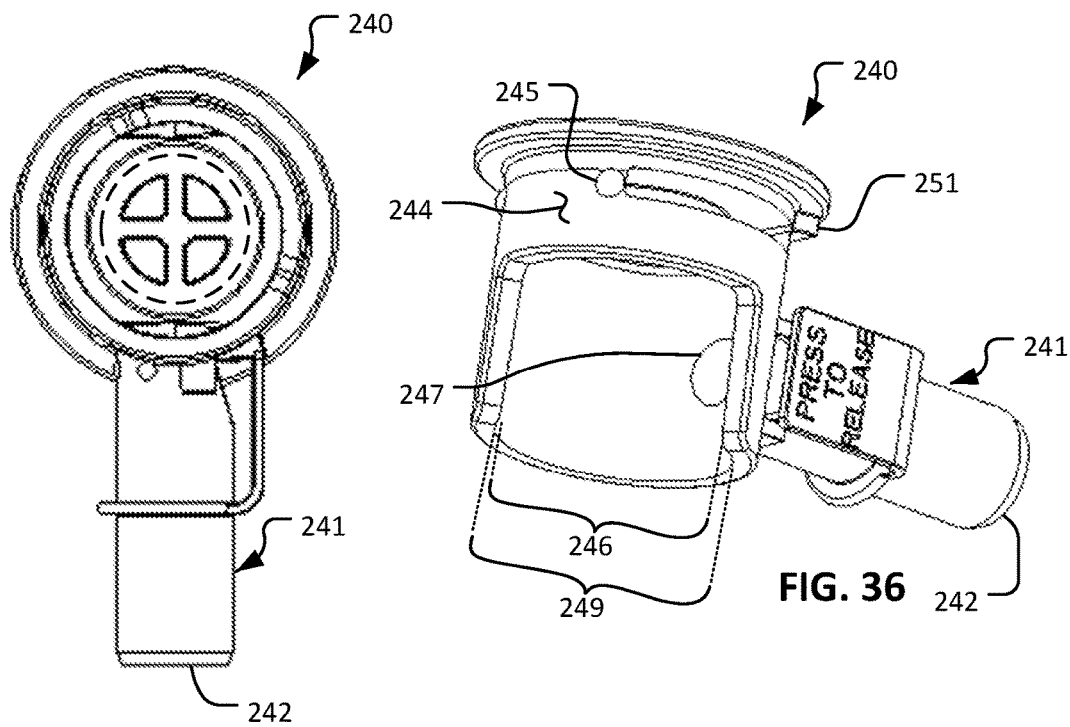
FIG. 37
FIG. 38
FIG. 39
FIG. 36

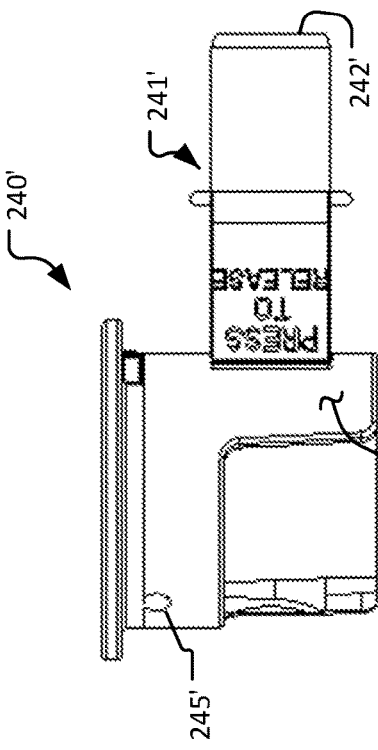
FIG. 53
FIG. 52
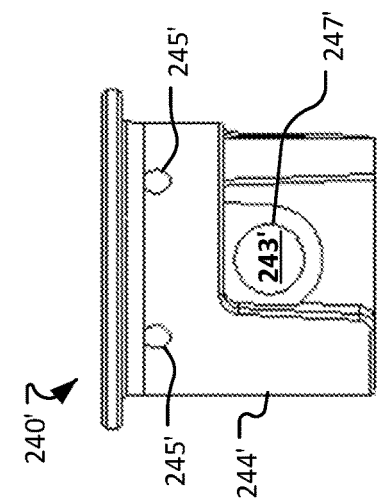
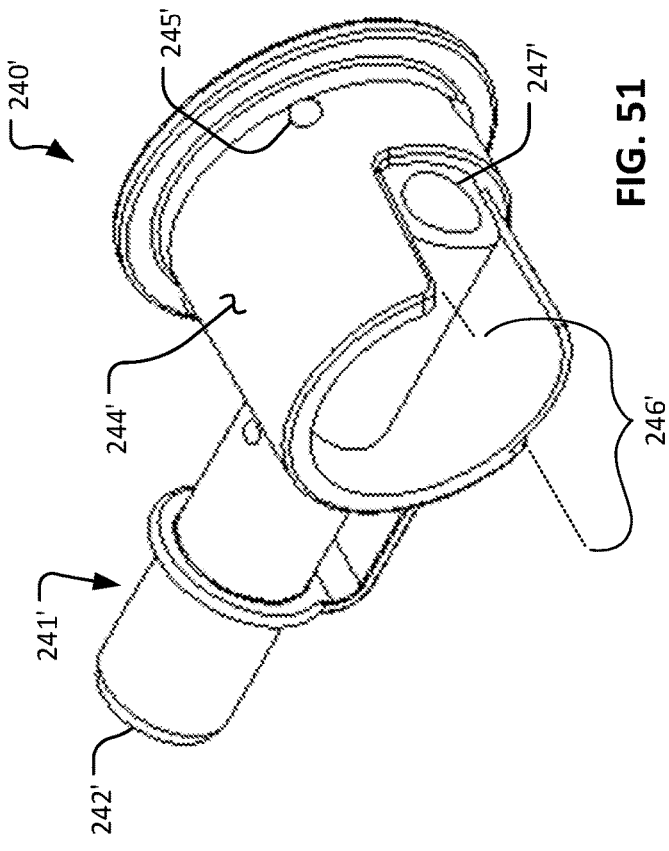
FIG. 51
FIG. 54

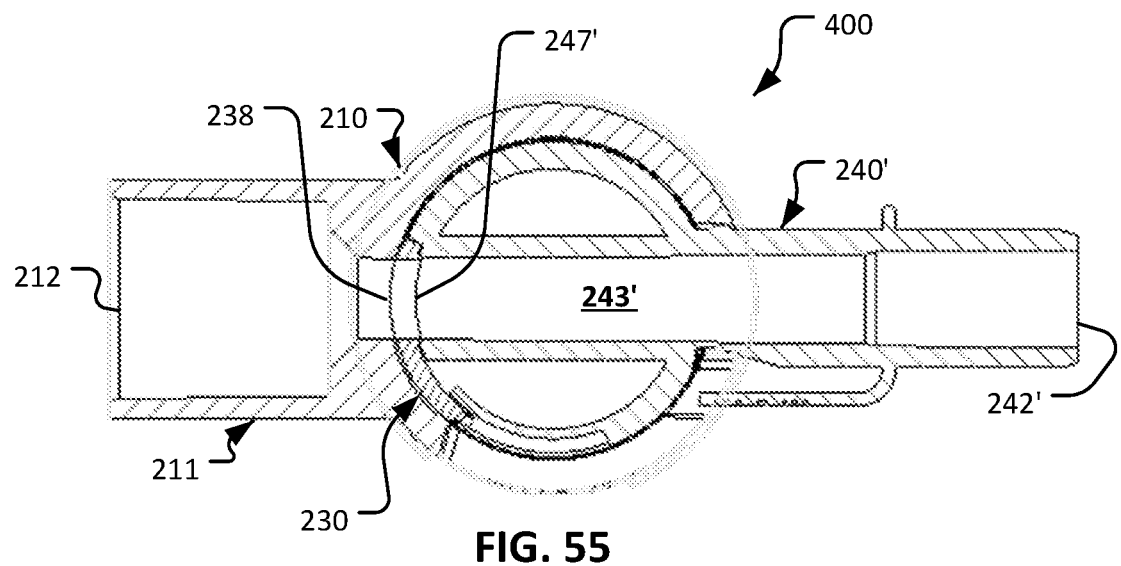
FIG. 55
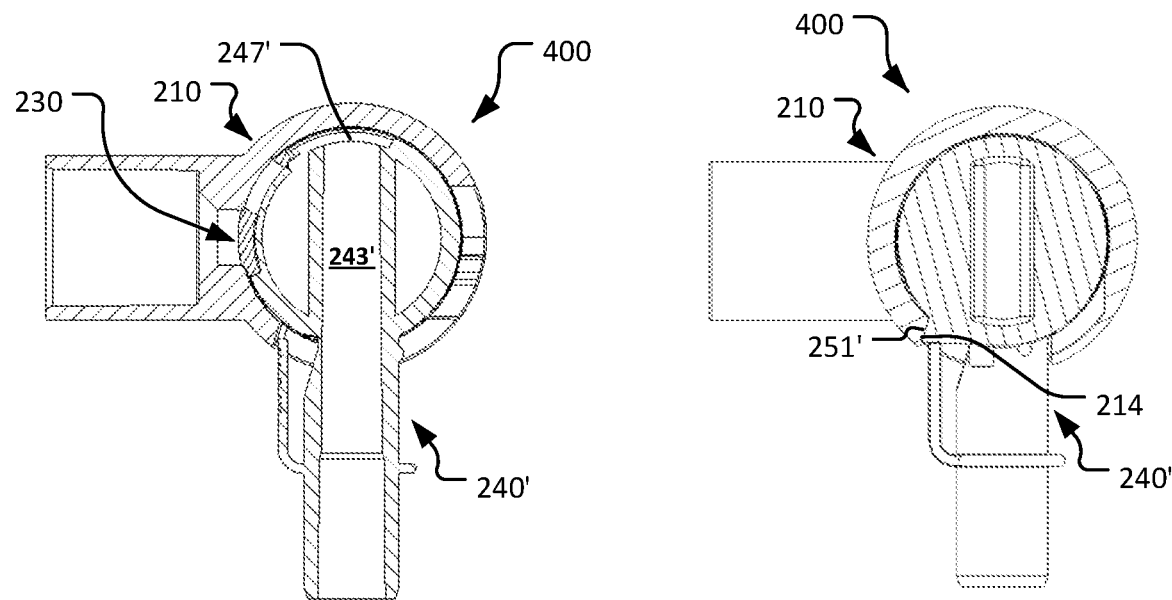
FIG. 56
FIG. 57

FLUID HANDLING DEVICES

CROSS-REFERENCE TO RELATED APPLICATIONS

This application is a National Stage application under 35 U.S.C. § 371 of International Application No. PCT/US2018/053410, having an International Filing Date of Sep. 28, 2018, which claims priority to U.S. application Ser. No. 62/659,473, filed on Apr. 18, 2018 and U.S. application Ser. No. 62/564,726, filed Sep. 28, 2017. The disclosure of the prior applications are considered part of the disclosure of this application, and are incorporated in their entirety into this application.

BACKGROUND

1. Technical Field

This document relates to fluid handling devices for use in fluid systems. For example, some embodiments described in this document relate to a quick disconnect type of fluid coupling device that inhibits fluid spillage during and after disconnection.

2. Background Information

Fluid systems commonly include components such as tubing, couplings, valves, pumps, reservoirs, filters, and the like. Such components can be connected together in a network to define a fluid flow path.

Fluid systems are often used in a medical context. Some examples of fluid systems used in the medical context include urinary drainage systems, wound drainage systems, infusion systems, respiratory systems, anesthesia systems, blood transfusion circuits, kidney dialysis systems, extracorporeal membrane oxygenation systems, extracorporeal circuits for heart/lung bypass, and the like. Some such medical fluid systems include the use of quick disconnect fluid coupling devices.

SUMMARY

This document describes fluid handling devices for use in fluid systems. For example, some embodiments described in this document relate to a quick disconnect type of fluid coupling device that prevents, inhibits, or minimizes fluid spillage during and after disconnection. For example, particular embodiments of these fluid coupling devices can be configured to improve medical fluid handling equipment because the fluid coupling devices can be connected and disconnected (e.g., multiple times) while minimizing fluid spillage. In the context of this disclosure, the term "fluid" includes both gases and liquids.

In one aspect, this disclosure is directed to a fluid handling device that includes a first body portion defining a first lumen extending between a first port and a first aperture, and a second body portion defining a second lumen extending between a second port and a second aperture. The first and second body portions are: (i) coupleable with each other and (ii) separable from each other. While the first and second body portions are separated from each other, the first and second apertures are each occluded. While the first and second body portions are coupled with each other, to the fluid handling device is configurable in: (a) a first coupled configuration in which an open flow path is defined between the first and second ports and (b) a second coupled configuration in which the first and second apertures are each occluded.

Such a fluid handling device may optionally include one or more of the following features. The first body portion may be movable in relation to the second portion to reconfigure the fluid handling device between the first and second coupled configurations. The first body portion may be pivotable in relation to the second portion to reconfigure the fluid handling device between the first and second coupled configurations. The fluid handling device may also include a core member pivotably coupled with the second body portion. Pivoting the first and second body portions between the first and second coupled configurations may cause the core member to pivot in relation to each of the first and second body portions. An engagement mechanism between the first body portion and the core member may limit how much the core member can pivot in relation to the first body portion. The fluid handling device may also include a core member movably coupled with the second body portion. The core member may define a central lumen. The open flow path may comprise the central lumen. The open flow path may be linear and unobstructed. While the first and second body portions are separated from each other, each end of the central lumen may be occluded by the second body portion. The fluid handling device may also include a seal between the first body portion and the second body portion. The seal may include a first material in contact with a second material that is softer than the first material. The seal may prevent entrance of bio-contamination into the first and second lumens. The seal may prevent entrance of bio-contamination into the first and second lumens during reconfiguration of the fluid handling device between the first and second coupled configurations.

In another aspect, this disclosure is directed to a fluid handling device that includes: (i) a first body portion defining a first lumen extending between a first port and a first aperture; (ii) a second body portion defining a second lumen extending between a second port and a second aperture; and (iii) a core member defining a third lumen, the core member movably coupled with the second body portion. The first body portion is movably coupleable with the second body portion between: (i) a first coupled configuration in which the first, second, and third lumens are fluidly separated from each other and (ii) a second coupled configuration in which the first, second, and third lumens are in fluid communication with each other.

Such a fluid handling device may optionally include one or more of the following features. The first and second body portions may be: (i) coupleable with each other and (ii) separable from each other. While the first and second body portions are separated from each other, the first and second apertures may each be occluded. While the first and second body portions are separated from each other, each end of the third lumen may be occluded. The core member may be pivotably coupled with the second body portion. While the fluid handling device is in the second coupled configuration, the first, second, and third lumens may define an unobstructed linear flow path. The first body portion may be movable in relation to the second body portion by pivoting the first body portion in relation to the second body portion about a central axis. While the fluid handling device is in the first coupled configuration, the first and second body portions may be separable from each other by moving the first body portion along the central axis away from the second body portion. The first and second body portions may be inseparable from each other while unless the fluid handling device is in the first coupled configuration. Moving the first and second body portions between the first and second coupled configurations may cause the core member to pivot in relation to each of the first and second body portions. An engagement mechanism between the first body portion and the core member may limit how much the core member can pivot in relation to the first body portion. The fluid handling device may consist of four distinct components: (1) the first body portion, (2) the second body portion, (3) the core member, and (4) a seal.

In another aspect, this disclosure is directed to a fluid coupling component that includes: (a) a housing defining a cylindrical internal space and an L-shaped slot in a wall of the housing; (b) a fluid handling connection extending from the housing, the fluid handling connection defining a lumen extending between a port and an internal aperture positioned at a juncture of the lumen and the cylindrical internal space; and (c) a shut-off member within the internal space and pivotably coupled with the housing. The shut-off member is pivotable in relation to the housing between a first configuration in which the shut-off member occludes the internal aperture and a second configuration in which the shut-off member does not occlude the internal aperture.

In another aspect, this disclosure is directed to a fluid coupling component that includes: (1) a housing defining a cylindrical internal space, the housing also defining a first aperture and a slot in a wall of the housing; (2) a fluid handling connection extending from the housing, the fluid handling connection defining a first lumen extending between a port and an internal aperture positioned at a juncture of the lumen and the cylindrical internal space; and (3) a cylindrical core member within the internal space and pivotably coupled with the housing. The core member defines a second lumen extending laterally fully through the core member. The core member is pivotable in relation to the housing between a first configuration in which the core member occludes the internal aperture and a second configuration in which the first and second lumens are in fluid communication with each other.

Particular embodiments of the subject matter described in this document can be implemented to realize one or more of the following advantages. First, in some embodiments the fluid coupling devices described herein are configured to allow fluid flow therethrough, and subsequently to allow the coupling halves to be uncoupled and separated while minimizing spillage of the fluid. Such a low-spillage quick disconnect fluid coupling device can be used while advantageously mitigating contamination caused by spillage of fluids that can be messy or even hazardous (e.g., biohazardous, corrosive, etc.). Associated safety risks and clean-up costs can thereby be reduced or eliminated.

Second, in some embodiments the fluid coupling devices provided herein are configured to convey fluid flow with a minimized amount of pressure drop and flow restriction. For example, some embodiments of the fluid coupling device can be configured for connection to ¼ inch inside diameter tubing while also having a pressure drop that is similar to the pressure drop of an equivalent length of ¼ inch inside diameter tubing.

Third, in some embodiments, the fluid coupling systems may advantageously provide a user with audible and/or tactile feedback in response to the motions performed for physically connecting and disconnecting the two portions of the fluid coupling devices in relation to each other. Such audible and/or tactile feedback can provide the user with an efficient and conclusive indication or confirmation of the proper function and desired configuration of the fluid coupling devices.

Fourth, some embodiments are designed with fail-safe provisions. For example, the coupling halves of some embodiments are physically prevented from being separated unless the anti-spillage members are in place and active for the prevention of spillage.

Fifth, some embodiments of the fluid coupling devices provided herein are advantageously designed with a robust locking system. That is, when the two halves of the coupling system are operably connected with each other, they are also mechanically locked in place. In some embodiments, to release the lock, special user actions are required (e.g., a latch on the coupling must be depressed). Such a design may reduce the likelihood of unintentional disconnections.

Sixth, some embodiments have a user-friendly design that is intuitive to properly operate. Accordingly, minimal operator training is required, and user mistakes are minimized.

Seventh, the low-spillage quick disconnect devices described herein are designed to be manufacture-able at a low cost. For example, some embodiments include only four components. The components can be molded plastic items in some cases. Moreover, in some embodiments the components can be simply snapped together (manually or automatically) for a low-cost assembly process.

Unless otherwise defined, all technical and scientific terms used herein have the same meaning as commonly understood by one of ordinary skill in the art to which this disclosure pertains. In addition, the materials, methods, and examples of the embodiments described herein are illustrative only and not intended to be limiting.

The details of one or more embodiments of the invention are set forth in the accompanying drawings and the description herein. Other features, objects, and advantages of the invention will be apparent from the description and drawings, and from the claims.

DESCRIPTION OF THE DRAWINGS

FIG. 7 is a perspective view of a first body portion of the low-spillage quick disconnect fluid coupling of FIG. 2.

FIG. 8 is an end view of the first body portion of FIG. 7.

FIG. 9 is a side view of the first body portion of FIG. 7.

FIG. 10 is a top view of the first body portion of FIG. 7.

FIG. 15 is a perspective view of a second body portion of the low-spillage quick disconnect fluid coupling of FIG. 2.

FIG. 16 is an end view of the second body portion of FIG. 15.

FIG. 17 is a side view of the second body portion of FIG. 15.

FIG. 18 is a top view of the second body portion of FIG. 15.

FIG. 36 is a perspective view of a second body portion of the low-spillage quick disconnect fluid coupling of FIG. 23.

FIG. 37 is an end view of the second body portion of FIG. 36.

FIG. 38 is a cross-sectional side view of the second body portion of FIG. 36.

FIG. 39 is a bottom view of the second body portion of FIG. 36.

FIG. 51 is a perspective view of a second body portion of the low-spillage quick disconnect fluid coupling of FIG. 49.

FIG. 52 is an end view of the second body portion of FIG. 51.

FIG. 53 is a side view of the second body portion of FIG. 51.

FIG. 54 is another perspective view of the second body portion of FIG. 51.

FIG. 55 is a cross-sectional view of the low-spillage quick disconnect fluid coupling of FIG. 49. The coupling is shown in a first coupled configuration that defines an open flow path therethrough.

FIG. 56 is a cross-sectional view of the low-spillage quick disconnect fluid coupling of FIG. 49. The coupling is shown in a second coupled configuration that has a closed flow path through the low-spillage quick disconnect fluid coupling.

FIG. 57 is another cross-sectional view of the low-spillage quick disconnect fluid coupling of FIG. 49. The coupling is shown in a second coupled configuration that has a hard stop member abutting a hard stop surface.

Like reference numbers represent corresponding parts throughout.

DETAILED DESCRIPTION OF ILLUSTRATIVE EMBODIMENTS

Figure 1:
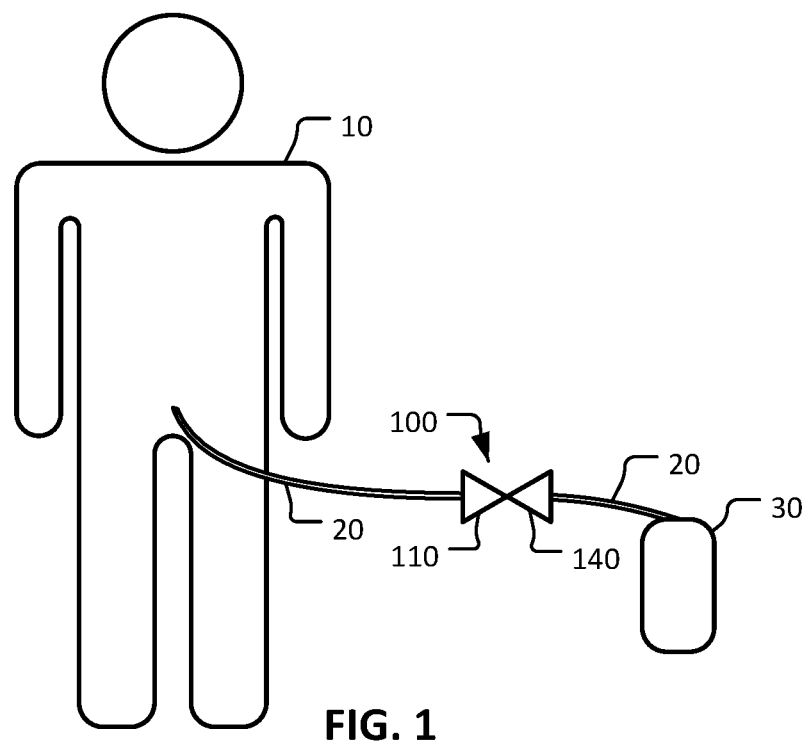
FIG. 1 is a schematic diagram of a human being that is connected to a urinary drainage system including an in-line low-spillage quick disconnect fluid coupling in accordance with some embodiments described herein.

The low-spillage quick disconnects described herein can be used in a variety of different implementations. For example, referring to FIG. 1, in some cases a low-spillage quick disconnect 100 as described herein can be used in a medical setting. In the depicted example, the low-spillage quick disconnect 100 is being used along a urine drainage line 20 between a patient 10 and a fluid collection bag 30.

Eventually, the fluid collection bag 30 will need to be emptied (e.g., by a nurse, healthcare aide, or other type of patientcare attendant). While the bag 30 needs to be emptied, the patient-end of the urine drainage line 20 usually needs to stay in place relative to the patient 10. The low-spillage quick disconnect 100 can be particularly useful in such a situation.

To disconnect the fluid collection bag 30 from being attached to the patient 10 by the urine drainage line 20, the low-spillage quick disconnect 100 can be opened (e.g., disconnected, separated, or decoupled). In particular, a first body portion 110 of the low-spillage quick disconnect 100 can be uncoupled from and separated from a second body portion 140 of the low-spillage quick disconnect 100. When the body portions 110 and 140 are separated (as described further below), the low-spillage design features of the low-spillage quick disconnect 100 come into use. That is, while body portions 110 and 140 are separated, apertures of the body portions 110 and 140 that would otherwise be open are instead occluded to inhibit or prevent fluid spillage from the body portions 110 and 140.

Figure 2:
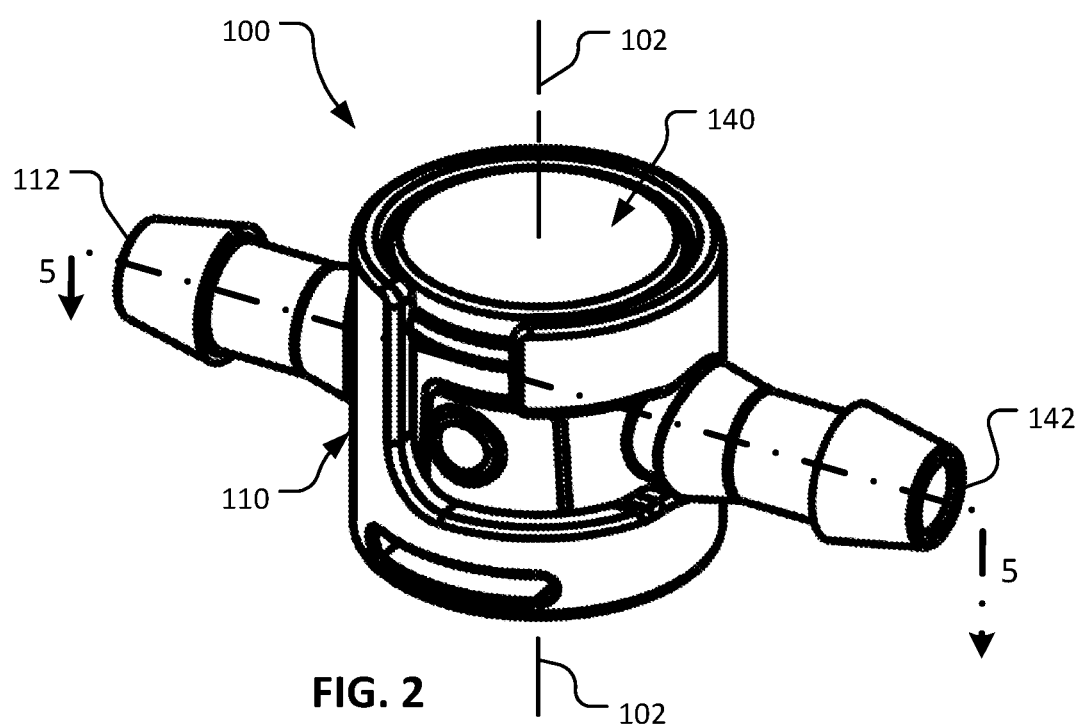
FIG. 2 is a perspective view of an example low-spillage quick disconnect fluid coupling in accordance with some embodiments. The low-spillage quick disconnect fluid coupling, as shown, is arranged in a coupled configuration that defines an open flow path through the low-spillage quick disconnect fluid coupling.

Referring to FIG. 2, an example embodiment of the low-spillage quick disconnect 100 is shown in a first coupled configuration. In this first coupled configuration, an open flow path exists between a first port 112 of the first body portion 110 and a second port 142 of the second body portion 140. While the depicted embodiment of the low-spillage quick disconnect 100 includes barbed connections for coupling with a flexible tube or hose, it should be understood that any type of fluid handling connection can be used. For example, connections such as, but not limited to, tube stems, bond ports, a barbed fitting (as shown), a luer fitting, a compression fitting, a quick disconnect fitting, a threaded fitting (internal or external), a sanitary fitting, a pigtail, a T-fitting, a Y-fitting, a bag fitment, and any other suitable type of configuration can be included such that the fluid coupling device 100 is suitable for connection to a fluid system as desired. In some embodiments, the low-spillage quick disconnect 100 may be supplied with removable caps (not shown), or another type of component, that is releasably coupled with the ends that define the ports 112 and/or 142.

Figure 5:
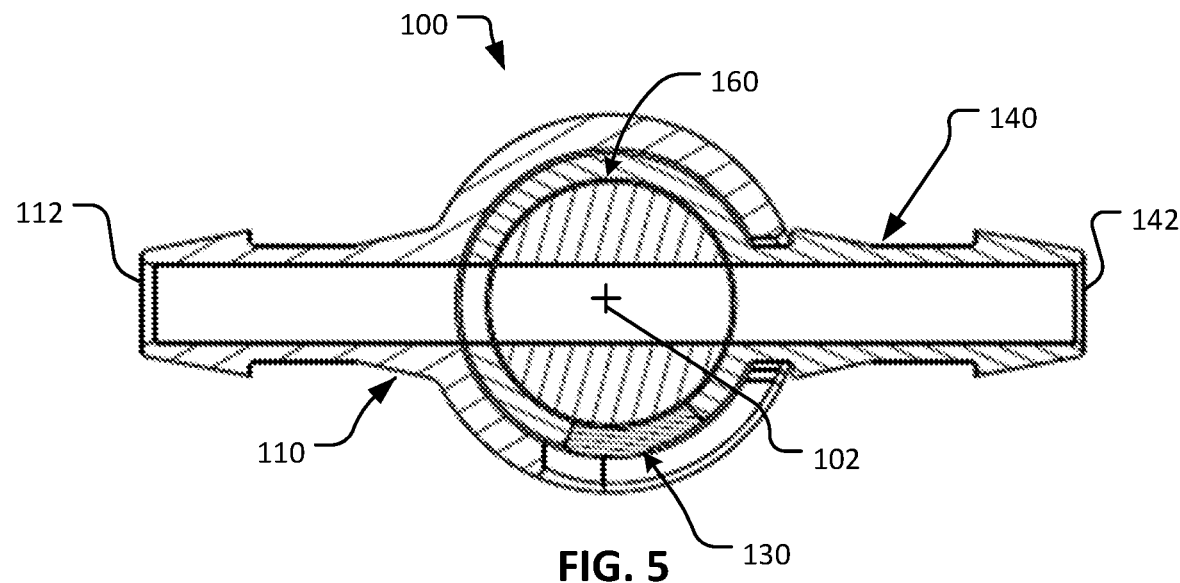
FIG. 5 is a cross-sectional view of the low-spillage quick disconnect fluid coupling of FIG. 2 in the configuration of FIG. 2.

Referring to FIG. 5, a longitudinal cross-section of the low-spillage quick disconnect 100 taken along section line 5-5 (as shown in FIG. 2) is illustrated. In this view, the open flow path between the first port 112 of the first body portion 110 and the second port 142 of the second body portion 140 is visible. It can also be seen that the open flow path through the low-spillage quick disconnect 100 is linear and unobstructed. Hence, the pressure drop and flow resistance through the low-spillage quick disconnect 100 is quite minimal.

The cross-sectional view of FIG. 5 also reveals two other internally-located components of the low-spillage quick disconnect 100. The two other components are a shut-off member 130 and a core member 160. The structures and functions of the shut-off member 130 and the core member 160 are described further below.

Figure 3:
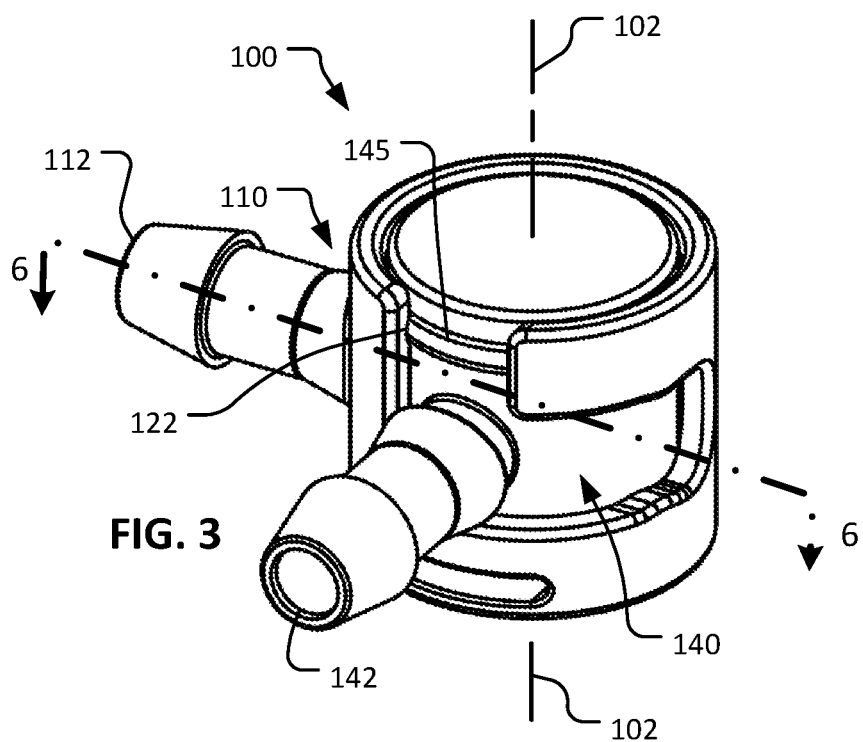
FIG. 3 is a perspective view of the low-spillage quick disconnect fluid coupling of FIG. 2. The low-spillage quick disconnect fluid coupling, as shown, is arranged in a coupled configuration in which no open flow path exists through the low-spillage quick disconnect fluid coupling.

Referring to FIG. 3, the low-spillage quick disconnect 100 can be reconfigured between the first coupled configuration as shown in FIG. 2 and a second coupled configuration as shown in FIG. 3. The body portions 110 and 140 are movably coupled with each other to facilitate the reconfiguration between the first and second coupled configurations. In fact, a close comparison of the first and second configurations reveals that, in the depicted embodiment, the body portions 110 and 140 are pivotably or rotatably coupled with each other, and therefore rotatable relative to each other about a central axis 102. The axis 102 is perpendicular to the open flow path defined between the first port 112 of the first body portion 110 and the second port 142 of the second body portion 140 (while the low-spillage quick disconnect 100 is in the first coupled configuration as shown in FIGS. 2 and 5).

In the depicted second coupled configuration, there is not an open flow path defined between the first port 112 and the second port 142. Rather, the flow or the potential for flow through the low-spillage quick disconnect 100 is, occluded, stopped or blocked when the low-spillage quick disconnect 100 is configured in the second coupled configuration.

Figure 6:
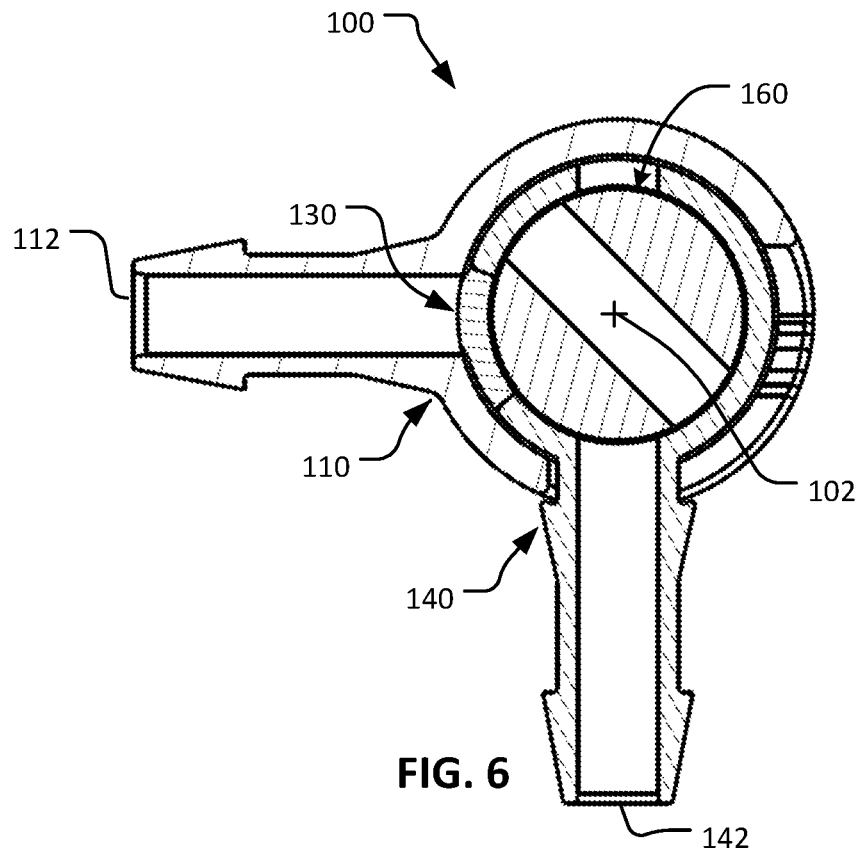
FIG. 6 is a cross-sectional view of the low-spillage quick disconnect fluid coupling of FIG. 2 in the configuration of FIG. 3.
Figure 11:
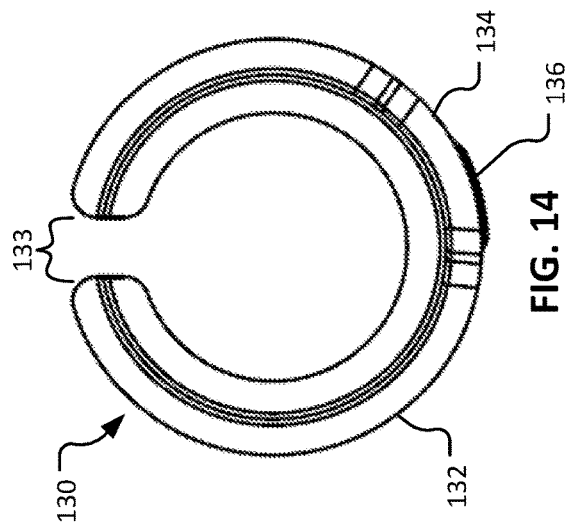
FIG. 11 is a perspective view of a shut-off member of the low-spillage quick disconnect fluid coupling of FIG. 2.
Figure 14:
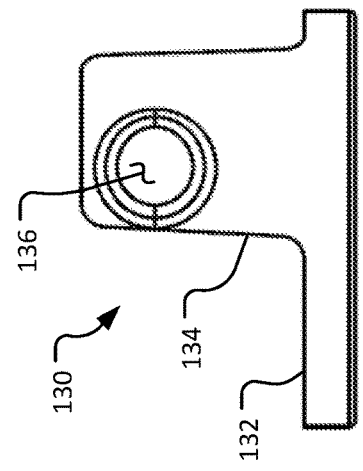
FIG. 14 is a top view of the shut-off member of FIG. 11.
Figure 13:
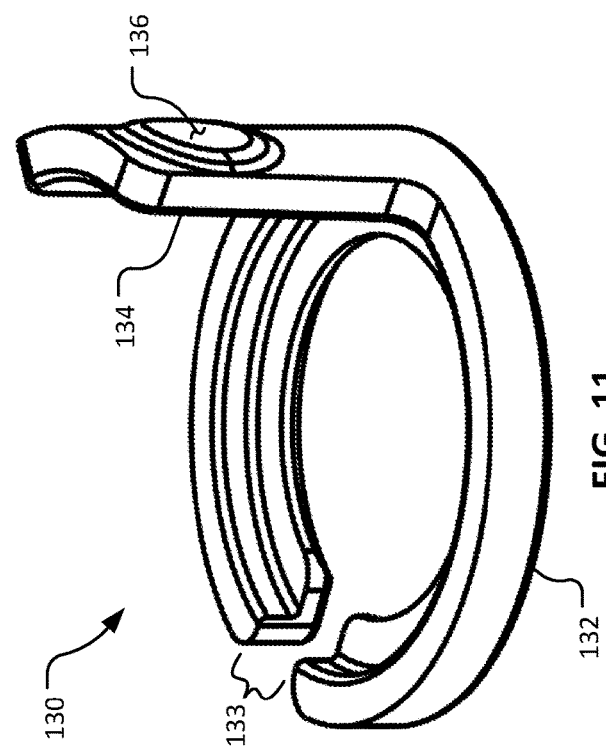
FIG. 13 is a side view of the shut-off member of FIG. 11.
Figure 12:
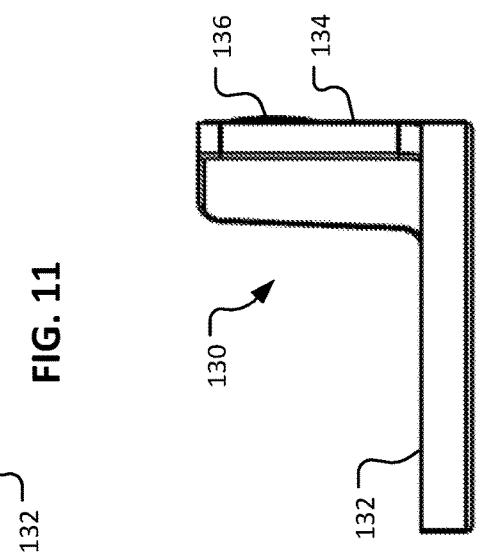
FIG. 12 is an end view of the shut-off member of FIG. 11.
Figure 22:
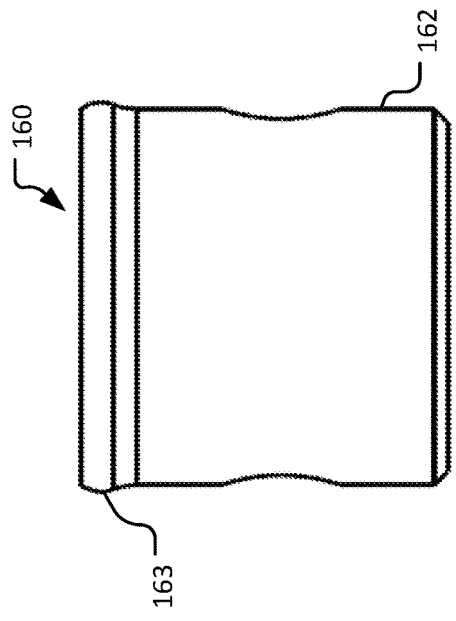
FIG. 22 is another side view of the core member of FIG. 19.
Figure 19:
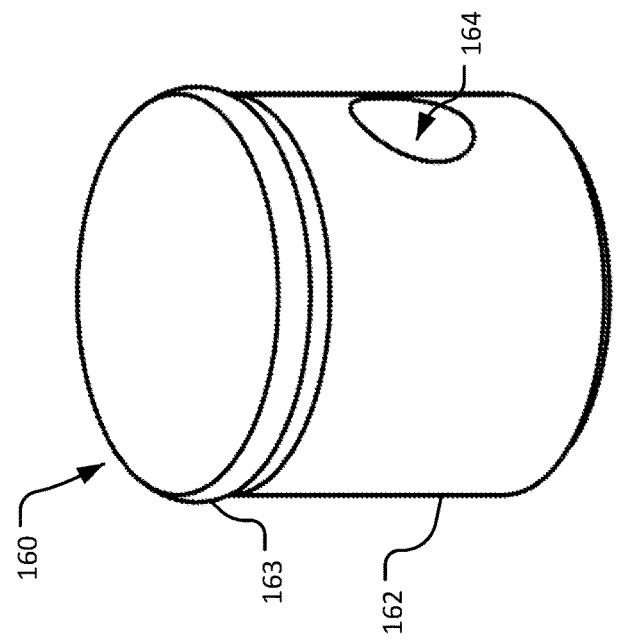
FIG. 19 is a perspective view of a core member of the low-spillage quick disconnect fluid coupling of FIG. 2.
Figure 20:
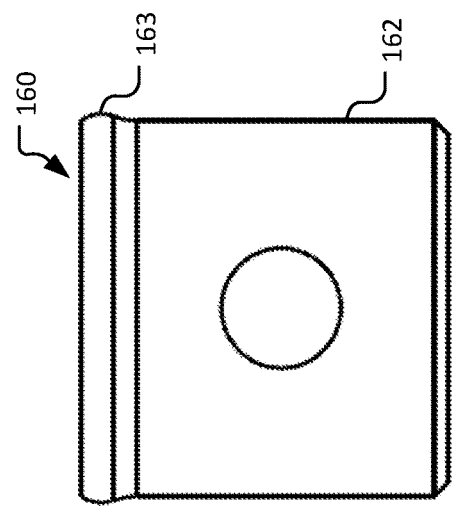
FIG. 20 is a side view of the core member of FIG. 19.
Figure 21:
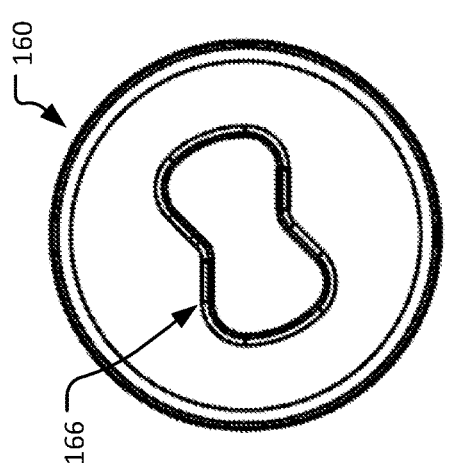
FIG. 21 is a bottom view of the core member of FIG. 19.

Referring to FIG. 6, a longitudinal cross-section of the low-spillage quick disconnect 100 taken along section line 6-6 (as shown in FIG. 3) is illustrated. In this view, it can be seen that there is no open flow path between the first port 112 of the first body portion 110 and the second port 142 of the second body portion 140. Rather, the lumen defined by the first body portion 110 is occluded by the shut-off member 130, and the lumen defined by the second body portion 140 is occluded by the core member 160.

A comparison between the longitudinal cross-sectional views of FIGS. 5 and 6 reveals that, while the body portions 110 and 140 have been rotated in relation to each other by a particular angular amount (e.g., about 90 degrees in the depicted embodiment), the core member 160 has rotated by less than that particular angular amount (e.g., the core member has rotated by about 45 degrees in the depicted embodiment). These functional relationships between the components of the low-spillage quick disconnect 100 contribute to the low-spill characteristics of the low-spillage quick disconnect 100, and will be described further below.

Figure 4:
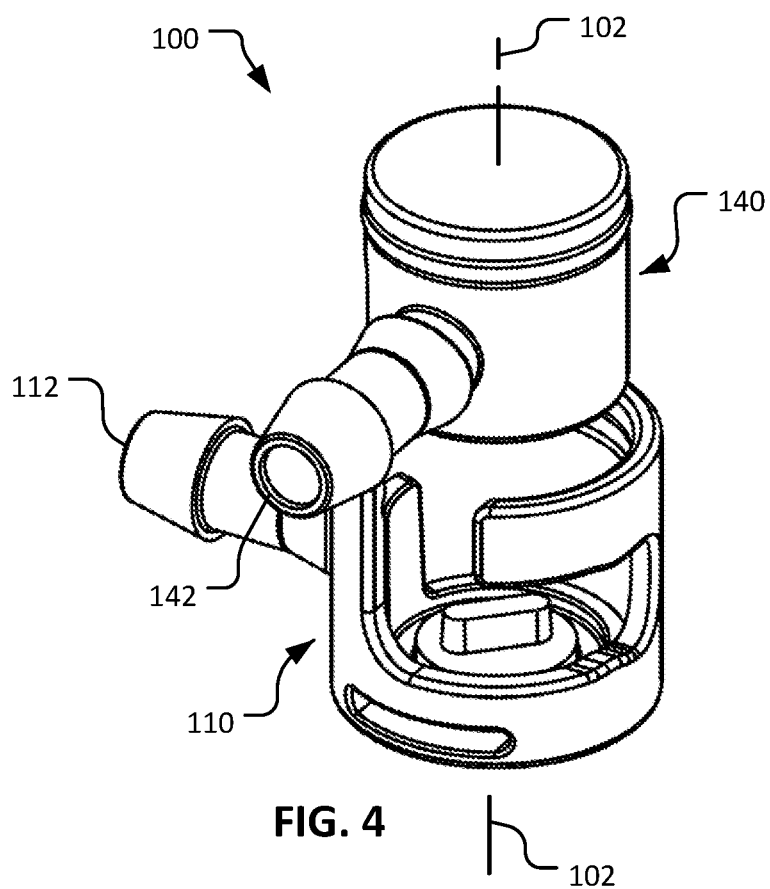
FIG. 4 is a perspective view of the low-spillage quick disconnect fluid coupling of FIG. 2. The low-spillage quick disconnect fluid coupling, as shown, is arranged in an uncoupled configuration.

Referring to FIG. 4, the body portions 110 and 140 of the low-spillage quick disconnect 100 are manually separable from each other. That is, when the low-spillage quick disconnect 100 is in the second coupled configuration (e.g., as shown in FIGS. 3 and 6), the body portions 110 and 140 can be separated from each other by moving them apart from each other along the central axis 102.

One of ordinary skill in the art will readily envision that separated body portions 110 and 140 can be recoupled to each other in order to reconnect them in a fluid system, and to reestablish fluid flow through the low-spillage quick disconnect 100. Of course, the process of coupling or recoupling separated body portions 110 and 140 is simply the reverse of the decoupling process.

While the body portions 110 and 140 are being separated, and while the body portions 110 and 140 remain separated, fluids in the body portions 110 and 140 are retained therein (assuming, of course, that tubes connected at ports 112 and 142 remain in place). In other words, while the body portions 110 and 140 are separated, spillage of fluid from the body portions 110 and 140 is inhibited and substantially prevented.

While the body portions 110 and 140 are separated, the shut-off member 130 is retained in a coupled arrangement with the first body portion 110, and the core member 160 is retained in a coupled arrangement with the second body portion 140. Accordingly, while the body portions 110 and 140 are separated, the lumen defined by the first body portion 110 is occluded by the shut-off member 130, and the lumen defined by the second body portion 140 is occluded by the core member 160 (as seen in FIG. 6). The occlusion provided by the shut-off member 130 and the core member 160 inhibits and substantially prevents spillage from the body portions 110 and 140 while they are separated from each other.

Referring to FIGS. 7-10, here an example first body portion 110 is shown in isolation from the other components of the low-spillage quick disconnect 100. Accordingly, greater detail of the first body portion 110 is now visible.

The first body portion 110 defines an internal space 120 that is shaped and sized to receive the second body portion 140 (FIGS. 15-18). Accordingly, the body portions 110 and 140 can be selectively mated and movably coupled with each other as described in reference to FIGS. 2 and 3.

An annular groove 122 is defined circumferentially along an inner wall of the first body portion 110 within the internal space 120. The annular groove 122 is shaped and sized to releasably engage with, and slidingly mate with, a corresponding annular protrusion located around a circumference of the second body portion (as described further below in reference to FIGS. 15-18). Accordingly, when the body portions 110 and 140 are pushed into engagement with each other, auditory and/or tactile feedback may be generated as a result of the engagement of the annular groove 122 and the annular protrusion. Simply stated, the two body portions 110 and 140 may snap together, for example. Additionally, the engagement of the annular groove 122 and the annular protrusion can serve to releasably detain the body portions 110 and 140 in the second coupled arrangement (FIG. 3). Accordingly, separation of the body portions 110 and 140 (as depicted in FIG. 4) necessitates an intentional action by a user of the low-spillage quick disconnect 100.

The first body portion 110 also defines an L-shaped slot 124. The L-shaped slot 124 is sized and shaped to define a clearance pathway that slidingly receives the fluid handling connection 141 (FIGS. 15-18) of the second body portion 140. The pathway defined by the L-shaped slot 124 facilitates both: (i) the relative movements of the body portions 110 and 140 between the uncoupled/separated arrangement as shown in FIG. 4 and the second coupled configuration as shown in FIG. 3, and (ii) the relative movements of the body portions 110 and 140 between the first coupled arrangement as shown in FIG. 2 and the second coupled arrangement as shown in FIG. 3. Additionally, the L-shaped slot 124 prevents separation of the body portions 110 and 140 unless the low-spillage quick disconnect 100 is in the second coupled configuration as shown in FIG. 3. Accordingly, the L-shaped slot 124 prevents separation of the body portions 110 and 140 unless the lumens defined within the low-spillage quick disconnect 100 are occluded. In this manner, the L-shaped slot 124 provides a fail-safe feature.

In the depicted embodiment, the terminal end (closed end or dead end) of the L-shaped slot 124 is shaped to create a detent position 125 where the fluid handling connection 141 (FIGS. 15-18) of the second body portion 140 will snap into place. While the fluid handling connection 141 of the second body portion 140 is in that detent position 125, the body portions 110 and 140 are arranged in the first configuration (FIGS. 2 and 5) such that the open flow path exists between the first port 112 of the first body portion 110 and the second port 142 of the second body portion 140. Accordingly, the detent position 125 provides auditory and/or tactile feedback that the low-spillage quick disconnect 100 is arranged in the first configuration (which operatively allows for fluids to flow therethrough).

The first body portion 110 also includes a mechanism that engages with the core member 160 (FIGS. 19-22). For example, in the depicted embodiment the first body portion 110 includes a projection 126 (like a mechanical key member) that engages with a corresponding recess 166 defined by the core member 160 (as described further below in reference to FIG. 21). The mechanical interaction between the projection 126 and the corresponding recess defined by the core member 160 serves to limit how much the core member 160 can rotate or pivot in relation to the first body portion 110.

In some embodiments, the first body portion 110 (and/or one or more other components of the low-spillage quick disconnect 100) is made of a thermoplastic material. In particular embodiments, the first body portion 110 is made of a thermoplastic, such as, but not limited to, polycarbonate, polysulfone, polyether ether ketone, polysulphide, polyester, polyvinylidene fluoride (PVDF), polyethylene, polyphenylsulfone (PPSU; e.g., Radel®), polyetherimide (PEI; e.g., Ultem®), polypropylene, polyphenylene, polyaryletherketone, Acrylonitrile butadiene styrene (ABS), and the like, and combinations thereof. In some embodiments, the first body portion 110 (or one or more portions thereof) is transparent or translucent so that internal components and/or fluids are visible. In some embodiments, the first body portion 110 (or one or more portions thereof) are overmolded with a second type of moldable material. In some embodiments, the low-spillage quick disconnect 100 is entirely metallic-free. That is, in some embodiments no metallic materials are included in the low-spillage quick disconnect 100. In some embodiments, one or more of the components of the low-spillage quick disconnect 100 (e.g., the first body portion 110, the second body portion 140, etc.) are made of metals such as, but not limited to, stainless steel, brass, aluminum, beryllium copper, and the like.

In some embodiments, the inner wall 121 (or portions thereof) that defines the internal space 120 is overmolded or coated with a softer material that seals against the second body portion 140 and/or the shut-off member 130 (which can each be made of harder materials). For example, one or more portions of the inner wall 121 (or the majority thereof, or the entirety thereof) can be overmolded with a softer seal material such as, but not limited to, silicone, fluoroelastomers (FKM), ethylene propylene diene monomer (EPDM), thermoplastic elastomers (TPE), bursa, buna-N, thermoplastic vulcanizates (TPV), and the like. In some such embodiments, such a softer seal material is overmolded as an annular band around the aperture 128. Alternatively, some embodiments of the first body portion 110 include an o-ring seal member positioned around the aperture 128.

It should be understood that the inclusion of features to create one or more such seals between the first body portion 110 and the second body portion 140 and/or the shut-off member 130 can serve to maintain the sterility of a sterilized low-spillage quick disconnect 100 during storage and use. That is, such seal(s) prevents the entrance of bio-contamination between the first body portion 110 and the second body portion 140 and/or shut-off member 130 that could otherwise enter into the first and second lumens defined by the first and second body portions 110 and 140. The seal performs that role during storage, and also during reconfiguration of the low-spillage quick disconnect 100 between the first and second coupled configurations (as shown in FIGS. 2 and 3).

While the seal(s) described above is comprised of a soft material on the surface of the inner wall 121 which abuts against a harder material of the second body portion 140 and/or the shut-off member 130, in some embodiments the locations of the soft and hard materials can be reversed. That is, in some embodiments the inner wall 121 of the first body portion 110 can be a hard material and one or more portions (or an entirety) of surface of the second body portion 140 and/or the shut-off member 130 can be overmolded with a softer material.

The first body portion 110 also defines a first aperture 128 which is at an opposite end of the fluid handling connection 111 that defines the first lumen extending from the first port 112. When the first body portion 110 is separated from the second body portion 140 (as shown in FIG. 4), the first aperture 128 is occluded so that fluid spillage from the first body portion 110 is inhibited and substantially prevented.

Referring also to FIGS. 11-14, the shut-off member 130 is movably positioned within, and remains captured within, the internal space 120 so that it can occlude the first aperture 128 while the first body portion 110 is separated from the second body portion 140 (as shown in FIG. 4). The first body portion 110 defines an annular seal seat 129 that slidably receives a correspondingly-sized and shaped seal base 132 of the shut-off member 130.

In some embodiments, the first body portion 110 includes one or more tabs (not shown) that loosely abut the top surface of the annular seal base 132 to mechanically detain the shut-off member 130 in the first body portion 110. Indeed, the shut-off member 130 and the first body portion 110 remain coupled together during use (both while the body portions 110 and 140 are coupled, and while the body portions 110 and 140 are separated). In the depicted embodiment, the annular seal base 132 defines an optional split 133 (e.g., the annular seal base 132 is an open C-shape) to facilitate assembly of the shut-off member 130 to the first body portion 110.

Extending from the annular seal base 132 is a sidewall portion 134. The sidewall portion 134 is sized and shaped to releasably engage with a correspondingly-sized and shaped cutout defined by the second body portion 140 (as described further below in reference to FIGS. 15-18).

The sidewall portion 134 includes a sealing projection 136. The sealing projection 136 is sized and shaped to releasably engage with the first aperture 128 like a plug or a stopper. When the sealing projection 136 is engaged with the first aperture 128, a substantially fluid-tight seal is established (assuming an operating pressure that is consistent with the specifications of the particular low-spillage quick disconnect 100 being used).

While the depicted embodiment of the shut-off member 130 includes the sidewall portion 134 that is cantilevered from the annular seal base 132, alternative designs are also envisioned. For example, in some embodiments the sidewall portion 134 makes up a portion of a cylinder. That is, additional material is included such that, rather than having a cantilevered sidewall portion 134, the shut-off member 130 is shaped as a hollow cylinder and sidewall portion 134 is within or part of the wall of that hollow cylinder. Such a cylindrical design may provide advantages such as increased rigidity and shape-stability. In some such embodiments, the sidewall portion 134 can be thicker than other portions of the cylinder wall. That way the sidewall portion 134 can still mechanically engage with the second body portion 140 (as described further below). The optional split 133 can still be included in a cylindrical design. In such a case, the optional split 133 would be a notch out of the end of the cylinder.

The shut-off member 130 can be made of any of the materials described above in reference to the first body portion 110. Alternatively, or additionally, in some embodiments the shut-off member 130 (or portions thereof, e.g., by overmolding) is made of materials such as, but not limited to, silicone, FKM, bursa, buna-N, EPDM, TPE, TPV, and the like.

Referring to FIGS. 15-18, here an example second body portion 140 is shown in isolation from the other components of the low-spillage quick disconnect 100. Accordingly, greater detail of the second body portion 140 is now visible. The second body portion 140 can be made of any of the materials described above in reference to the first body portion 110.

The second body portion 140 includes a generally cylindrical body 144 that is configured to be releasably received within the internal space 120 defined by the first body portion 110 as shown in FIGS. 7 and 9. The second body portion 140 also includes a fluid handling connection 141 that can extend through the L-shaped slot 124 of the first body portion 110.

Reference will now be made to the physical features of the second body portion 140 that were mentioned above as being releasably engageable with corresponding-sized and shaped features of the first body portion 110 or the shut-off member 130. For example, the second body portion 140 includes an annular protrusion 145 that is shaped and sized to releasably engage with, and slidingly mate with, the annular groove 122 of the first body portion 110 (FIGS. 7-10). Additionally, the second body portion 140 includes a cutout 146 that is sized and shaped to releasably engage with the sidewall portion 134 of the shut-off member 130 (FIGS. 11-14). The engagement between the cutout 146 and the sidewall portion 134 ensures that rotations of the second body portion 140 in relation to the first body portion 110 also cause corresponding rotations of the shut-off member 130 in relation to the first body portion 110. That physical relationship between the cutout 146 and the sidewall portion 134 is visible by comparing the configurations of FIGS. 5 and 6 to each other.

While the depicted embodiment of the second body portion 140 includes the cutout 146, alternative designs are also envisioned. For example, in some embodiments the area of the cutout 146 can be a portion of the generally cylindrical body 144 with a thinner wall than other portions of the generally cylindrical body 144. Such a more completely cylindrical design of the second body portion 140 may provide advantages such as increased rigidity and shape-stability. Since the area of the cutout 146 would have a thinner wall than other portions of the generally cylindrical body 144, mechanical engagement between the second body portion 140 and the sidewall portion 134 of the shut-off member 130 would still be facilitated.

The generally cylindrical body 144 of the second body portion 140 also defines two apertures: (i) a second aperture 147 and (ii) a third aperture 148. Here the second aperture 147 and the third aperture 148 are referred to as "second" and "third" to distinguish them from the first aperture 128 of the first body portion 110, as described above. The second aperture 147 is at an opposite end of the fluid handling connection 141 that defines the second lumen extending from the second port 142. When the second body portion 140 is separated from the first body portion 110 (as shown in FIG. 4), the second aperture 147 is occluded so that fluid spillage from the second body portion 140 is inhibited and substantially prevented.

The generally cylindrical body 144 of the second body portion 140 also defines an internal space 149. The internal space 149 is generally cylindrical. The cutout 146, the second aperture 147, and the third aperture 148 are open to the internal space 149.

Referring also to FIGS. 19-22, the core member 160 includes a generally cylindrical body 162 that can be movably positioned within internal space 149 so that it can occlude the second aperture 147 and the third aperture 148 while the second body portion 140 is separated from the first body portion 110 (as shown in FIG. 4).

The core member 160 can be made of any of the materials described above in reference to the first body portion 110. Alternatively, or additionally, in some embodiments the core member 160 (or portions thereof, e.g., by overmolding) is made of materials such as, but not limited to, silicone, buna, buna-N, FKM, EPDM, TPE, TPV, and the like.

In some embodiments, the core member 160 can include an annular protrusion 163. The annular protrusion 163 can be sized and shaped to releasably engage with, and slidingly mate with, a corresponding annular groove (not visible) that is defined circumferentially around an inner wall of the internal space 149 of the second body portion 140. Engagement of the annular protrusion 163 within such an annular groove can ensure that the core member 160 remains coupled within the internal space 149 of the second body portion 140 while also being rotatably movable relative to the second body portion 140.

The core member 160 defines a third lumen 164 that extends laterally fully through the generally cylindrical body 162. Depending on the relative rotational position of the core member 160 in relation to the second body portion 160, the third lumen 164 of the core member 160 can serve as a fluid flow path between the second and third apertures 147 and 148. That is, when the third lumen 164 is in alignment with the second and third apertures 147 and 148, the third lumen 164 provides a fluid flow path between the second and third apertures 147 and 148 (and also between the first and second ports 112 and 142 which is through an entirety of the low-spillage quick disconnect 100). Such alignment exists while the low-spillage quick disconnect 100 is in the first coupled configuration (FIGS. 2 and 5).

When the core member 160 is rotated in relation to the second body portion 140 such that the third lumen 164 is not in alignment with the second and third apertures 147 and 148, then the core member 160 occludes the second and third apertures 147 and 148, and flow through the low-spillage quick disconnect 100 is prevented. Such an arrangement exists while the low-spillage quick disconnect 100 is in the second coupled configuration (FIGS. 3 and 6), and also while the first and second body portions 110 and 140 are separated from each other (FIG. 4). Moreover, while the third lumen 164 is not in alignment with the second and third apertures 147 and 148, then the third lumen 164 is itself also occluded at each end thereof by the inner wall of the second body portion 140.

The core member 160 also defines a recess 166. In the depicted embodiment, the recess 166 has a cross-sectional shape that resembles a bow tie. Like a mechanical key within a keyway, the recess 166 physically receives the projection 126 of the first body portion 110 (FIGS. 7-10), while defining additional clearance space there between. Since the recess 166 is larger than the projection 126, the mechanical interaction between the projection 126 and the recess 166 allows the core member 160 to rotate or pivot in relation to the first body portion 110, but also limits how much the core member 160 can rotate or pivot in relation to the first body portion 110.

The recess 166 can be designed to allow any desired amount of relative rotation between the core member 160 and the first body portion 110. In the depicted embodiment, about 45 degrees of relative rotation is allowed by the mechanical interaction of the recess 166 and the projection 126. In some embodiments, an allowed relative rotation between the core member 160 and the first body portion 110 is within a range of about 40 degrees to about 50 degrees, or about 35 degrees to about 55 degrees, or about 30 degrees to about 60 degrees.

Figure 23:
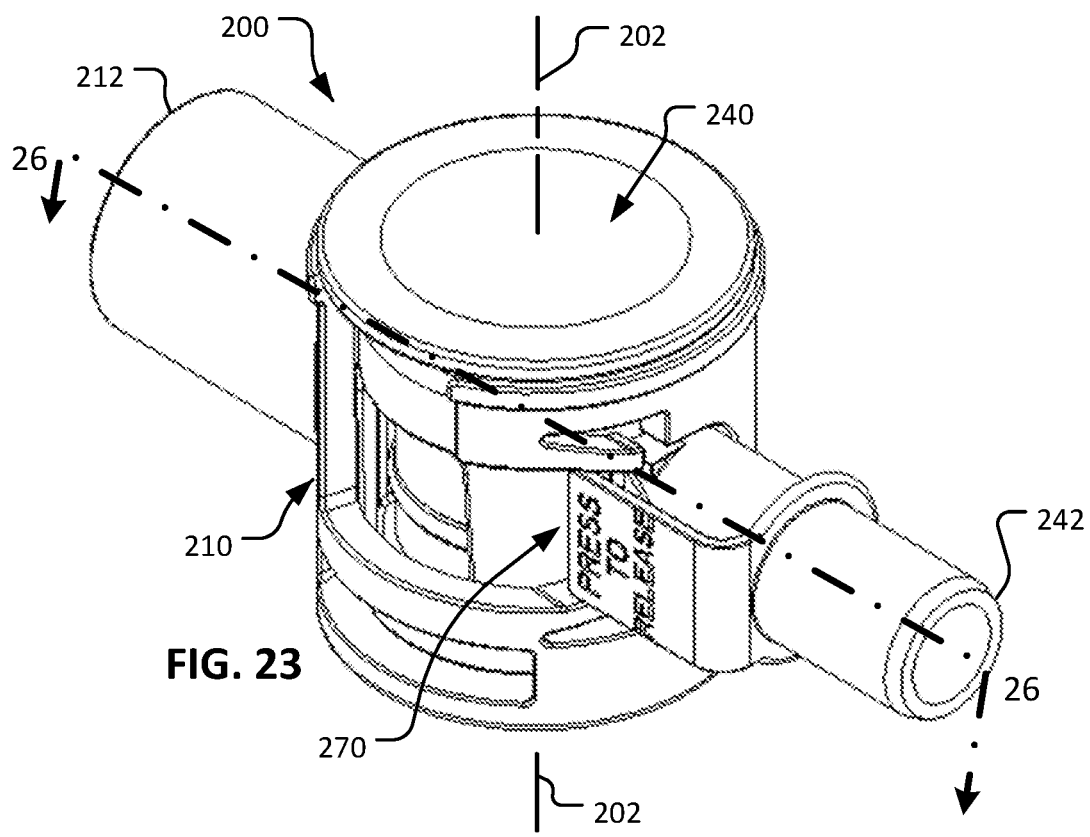
FIG. 23 is a perspective view of another example low-spillage quick disconnect fluid coupling in accordance with some embodiments. The low-spillage quick disconnect fluid coupling, as shown, is arranged in a coupled configuration that defines an open flow path through the low-spillage quick disconnect fluid coupling.

Referring to FIG. 23, another example embodiment of a low-spillage quick disconnect 200 is shown in a first coupled configuration. In this first coupled configuration, an open flow path exists between a first port 212 of the first body portion 210 and a second port 242 of the second body portion 240. While the depicted embodiment of the low-spillage quick disconnect 200 includes sleeve, socket, or nipple connections for coupling with a flexible tube or hose, it should be understood that any type of fluid handling connection can be used. For example, connections such as, but not limited to, barbed connections, bond ports, a luer fitting, a compression fitting, a quick disconnect fitting, a threaded fitting (internal or external), a sanitary fitting, a pigtail, a T-fitting, a Y-fitting, a bag fitment, and any other suitable type of configuration can be included such that the fluid coupling device 200 is suitable for connection to a fluid system as desired. In some embodiments, the low-spillage quick disconnect 200 may be supplied with removable caps and/or plugs (not shown), or another type of component, that is releasably coupled with the ends that define the ports 212 and/or 242.

Figure 26:
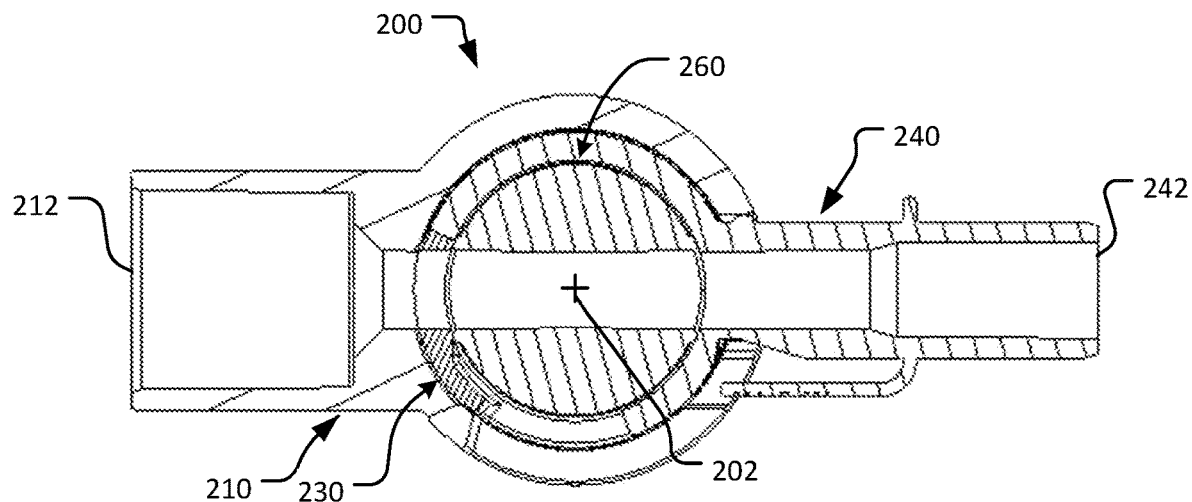
FIG. 26 is a cross-sectional view of the low-spillage quick disconnect fluid coupling of FIG. 23 in the configuration of FIG. 23.

Referring to FIG. 26, a longitudinal cross-section of the low-spillage quick disconnect 200 taken along section line 26-26 (as shown in FIG. 23) is illustrated. In this view, the open flow path between the first port 212 of the first body portion 210 and the second port 242 of the second body portion 240 is visible. It can also be seen that the open flow path through the low-spillage quick disconnect 200 is linear and unobstructed. Hence, the pressure drop and flow resistance through the low-spillage quick disconnect 200 is quite minimal.

The cross-sectional view of FIG. 26 also reveals two other internally-located components of the low-spillage quick disconnect 200. The two other components are a shut-off member 230 and a core member 260. The structures and functions of the shut-off member 230 and the core member 260 are described further below.

Figure 24:
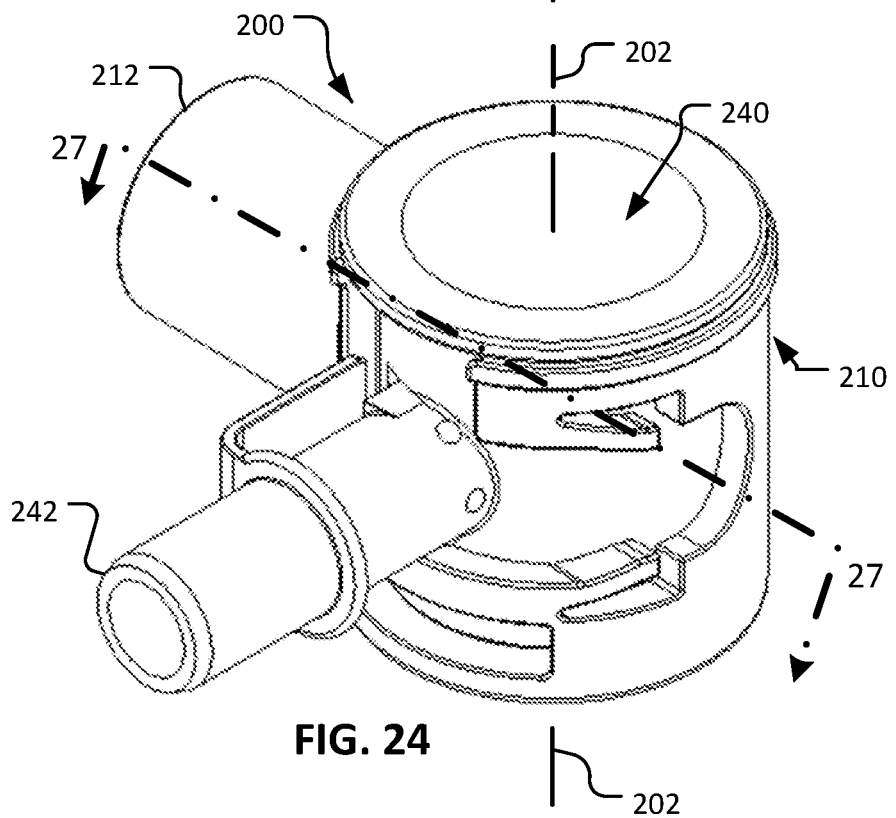
FIG. 24 is a perspective view of the low-spillage quick disconnect fluid coupling of FIG. 23. The low-spillage quick disconnect fluid coupling, as shown, is arranged in a coupled configuration in which no open flow path exists through the low-spillage quick disconnect fluid coupling.

Referring to FIG. 24, the low-spillage quick disconnect 200 can be reconfigured between the first coupled configuration as shown in FIG. 23 and a second coupled configuration as shown in FIG. 24. The body portions 210 and 240 are movably coupled with each other to facilitate the reconfiguration between the first and second coupled configurations. In fact, a close comparison of the first and second configurations reveals that, in the depicted embodiment, the body portions 210 and 240 are pivotably or rotatably coupled with each other, and therefore rotatable relative to each other about a central axis 202. The axis 202 is perpendicular to the open flow path defined between the first port 212 of the first body portion 210 and the second port 242 of the second body portion 240 (while the low-spillage quick disconnect 200 is in the first coupled configuration as shown in FIGS. 23 and 26).

The depicted embodiment of the low-spillage quick disconnect 200 includes an optional latch mechanism 270. When the low-spillage quick disconnect 200 is in the first coupled configuration (as shown in FIG. 23), the latch mechanism 270 detains the body portions 210 and 240 from rotating in relation to each other. That is, the body portions 210 and 240 cannot be rotated relative to each other (e.g., to reconfigure the low-spillage quick disconnect 200 to the second coupled configuration as shown in FIG. 24) unless the latch mechanism 270 is affirmatively acted upon to unlatch or deactivate the latch mechanism 270. Accordingly, the latch mechanism 270 can safeguard against an accidental or unintentional closing of the open flow path defined between the first port 212 and the second port 242 that exists while the low-spillage quick disconnect 200 is in the first coupled configuration as shown in FIG. 23. When the latch mechanism 270 is affirmatively acted upon to deactivate it, then the body portions 210 and 240 can be pivoted in relation to each other to reconfigure the low-spillage quick disconnect 200 from the first coupled configuration as shown in FIG. 23 to the second coupled configuration as shown in FIG. 24. In the depicted embodiment, the latch mechanism is deactivated by depressing a tab, as described further below.

Still referring to FIG. 24, in the depicted second coupled configuration, there is not an open flow path defined between the first port 212 and the second port 242. Rather, the flow or the potential for flow through the low-spillage quick disconnect 200 is, occluded, stopped or blocked when the low-spillage quick disconnect 200 is configured in the second coupled configuration.

Figure 27:
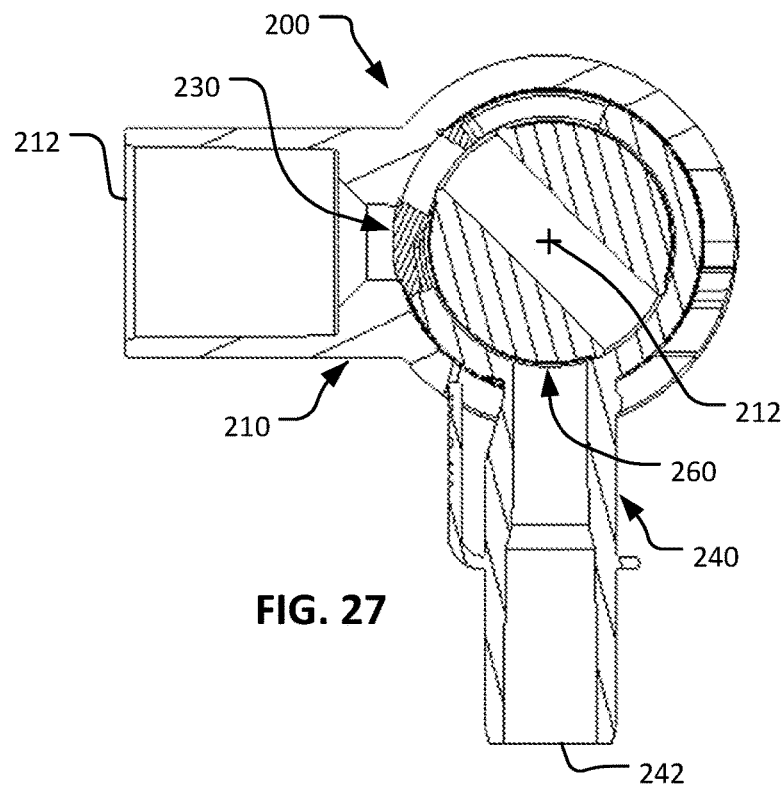
FIG. 27 is a cross-sectional view of the low-spillage quick disconnect fluid coupling of FIG. 23 in the configuration of FIG. 24.

Referring to FIG. 27, a longitudinal cross-section of the low-spillage quick disconnect 200 taken along section line 27-27 (as shown in FIG. 24) is illustrated. In this view, it can be seen that there is no open flow path between the first port 212 of the first body portion 210 and the second port 242 of the second body portion 240. Rather, the lumen defined by the first body portion 210 is occluded by the shut-off member 230, and the lumen defined by the second body portion 240 is occluded by the core member 260.

A comparison between the longitudinal cross-sectional views of FIGS. 26 and 27 reveals that, while the body portions 210 and 240 have been rotated in relation to each other by a particular angular amount (e.g., about 90 degrees in the depicted embodiment), the core member 260 has rotated by less than that particular angular amount (e.g., the core member has rotated by about 45 degrees in the depicted embodiment). In addition, while in the depicted embodiment the body portions 210 and 240 have been rotated in relation to each other by 90 degrees and the core member 260 has rotated by about 45 degrees, the shut-off member 230 has rotated by about 30 degrees. These functional relationships between the components of the low-spillage quick disconnect 200 contribute to the low-spill characteristics of the low-spillage quick disconnect 200, and will be described further below.

Figure 25:
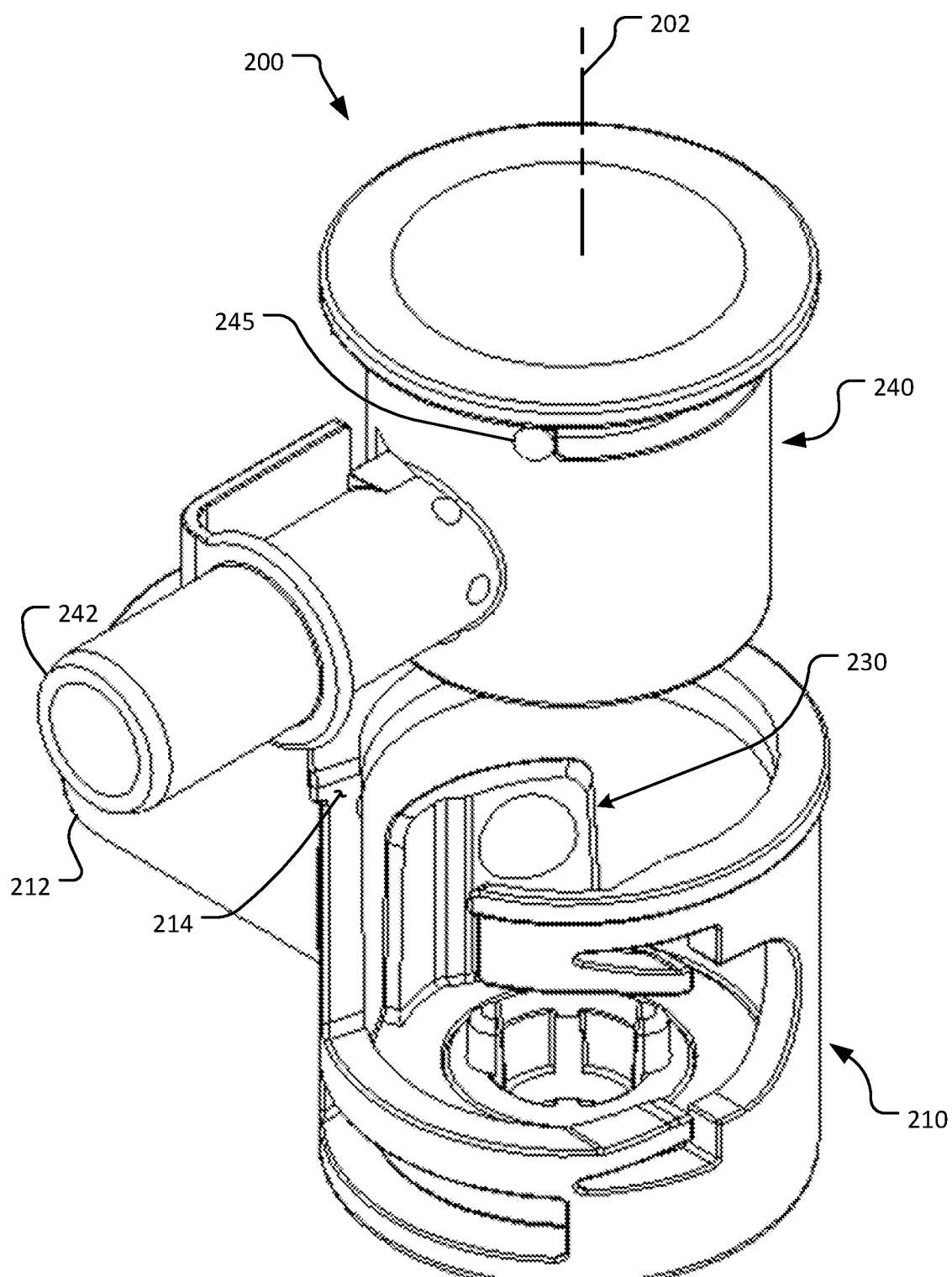
FIG. 25 is a perspective view of the low-spillage quick disconnect fluid coupling of FIG. 23. The low-spillage quick disconnect fluid coupling, as shown, is arranged in an uncoupled configuration.

Referring to FIG. 25, the body portions 210 and 240 of the low-spillage quick disconnect 200 are manually separable from each other. That is, when the low-spillage quick disconnect 200 is in the second coupled configuration (e.g., as shown in FIGS. 24 and 27), the body portions 210 and 240 can be separated from each other by moving them apart from each other along the central axis 202.

One of ordinary skill in the art will readily envision that separated body portions 210 and 240 can be recoupled to each other in order to reconnect them in a fluid system, and to reestablish fluid flow through the low-spillage quick disconnect 200. Of course, the process of coupling or recoupling separated body portions 210 and 240 is simply the reverse of the decoupling process.

While the body portions 210 and 240 are being separated, and while the body portions 210 and 240 remain separated, fluids in the body portions 210 and 240 are retained therein (assuming, of course, that tubes connected at ports 212 and 242 remain in place). In other words, while the body portions 210 and 240 are separated, spillage of fluid from the body portions 210 and 240 is inhibited and substantially prevented.

While the body portions 210 and 240 are separated, the shut-off member 230 is retained in a coupled arrangement with the first body portion 210, and the core member 260 (not visible) is retained in a coupled arrangement with the second body portion 240. Accordingly, while the body portions 210 and 240 are separated, the lumen defined by the first body portion 210 is occluded by the shut-off member 230, and the lumen defined by the second body portion 240 is occluded by the core member 260 (as seen in FIG. 27). The occlusion provided by the shut-off member 230 and the core member 260 inhibits and substantially prevents spillage from the body portions 210 and 240 while they are separated from each other.

Referring to FIGS. 28-31, here an example first body portion 210 is shown in isolation from the other components of the low-spillage quick disconnect 200. Accordingly, greater detail of the first body portion 210 is now visible.

The first body portion 210 defines an internal space 220 that is shaped and sized to receive the second body portion 240 (FIGS. 36-39). Accordingly, the body portions 210 and 240 can be selectively mated and movably coupled with each other as described in reference to FIGS. 23-27.

An annular groove 222 is defined circumferentially along an inner wall of the first body portion 210 within the internal space 220. The annular groove 222 is shaped and sized to releasably engage with, and slidingly mate with, one or more corresponding protrusions located on the second body portion 240 (as described further below in reference to FIGS. 36-39). In some embodiments, rather than the annular groove 222 the first body portion 210 includes one or more protrusions that extend inwardly into the internal space 220. In such a case, the second body portion 240 includes one or more corresponding grooves or slots that slidingly receive the protrusion(s) (as described further below in reference to FIGS. 36-39). Accordingly, when the body portions 210 and 240 are pushed into engagement with each other, auditory and/or tactile feedback may be generated as a result of the engagement of the annular groove 222 and the one or more protrusions of the second body portion 240. Simply stated, the two body portions 210 and 240 may snap together, for example, and a "click" sound and/or tactile feedback may be generated. Additionally, the engagement of the annular groove 222 and the one or more protrusions can serve to releasably detain the body portions 210 and 240 in the second coupled arrangement (FIG. 24). Accordingly, separation of the body portions 210 and 240 (as depicted in FIG. 25) necessitates an intentional action by a user of the low-spillage quick disconnect 200.

The first body portion 210 also defines an L-shaped slot 224. The L-shaped slot 224 is sized and shaped to define a clearance pathway that slidingly receives the fluid handling connection 241 (FIGS. 36-39) of the second body portion 240. The pathway defined by the L-shaped slot 224 facilitates both: (i) the relative movements of the body portions 210 and 240 between the uncoupled/separated arrangement as shown in FIG. 25 and the second coupled configuration as shown in FIG. 24, and (ii) the relative movements of the body portions 210 and 240 between the first coupled arrangement as shown in FIG. 23 and the second coupled arrangement as shown in FIG. 24. Additionally, the L-shaped slot 224 prevents separation of the body portions 210 and 240 unless the low-spillage quick disconnect 200 is in the second coupled configuration as shown in FIG. 24. Accordingly, the L-shaped slot 224 prevents separation of the body portions 210 and 240 unless the lumens defined within the low-spillage quick disconnect 200 are occluded. In this manner, the L-shaped slot 224 provides a fail-safe feature.

As part of the latch mechanism 270 (as described above in reference to FIG. 23), the first body portion 210 includes a first deflectable member 225a and a second deflectable member 225b. The first deflectable member 225a is positioned along one side of the L-shaped slot 224 and the second deflectable member 225b is positioned symmetrically along an opposing side of the L-shaped slot 224. The deflectable members 225a-b extend from other portions of the first body portion 210 like cantilevered beams. In their natural positions (undeflected), the distance between the free end portions of the deflectable members 225a-b is less than the distance between the ends of the deflectable members 225a-b that are attached to the other portions of the first body portion 210. As the two body portions 210 and 240 are rotated in relation to each other into the first coupled arrangement as shown in FIG. 23, physical interference between the fluid handling connection 241 (FIGS. 36-39) of the second body portion 240 and the deflectable members 225a-b causes the deflectable members 225a-b to flex in opposite directions (like cantilevered beams) outwardly away from the L-shaped slot 224. When the relative rotation between the body portions 210 and 240 reaches (or nearly reaches) its end of travel where the low-spillage quick disconnect 200 is in its first coupled configuration (FIG. 23), the fluid handling connection 241 clears the free ends of the deflectable members 225a-b and the deflectable members 225a-b snap back to their undeflected positions (as shown). When the deflectable members 225a-b snap back to their undeflected positions, the free end portions of the deflectable members 225a-b physically interfere with and block the fluid handling connection 241 from moving out of its position at the end of the L-shaped slot 224. The free end portions of the deflectable members 225a-b thereby detain or latch the low-spillage quick disconnect 200 in the first coupled configuration. An affirmative activation of the latch mechanism 270 is required to flex the deflectable members 225a-b out of the way of the fluid handling connection 241 so that the low-spillage quick disconnect 200 can be reconfigured away from the first coupled configuration.

When, after the fluid handling connection 241 pass by the deflectable members 225a-b and the deflectable members 225a-b snap back to their undeflected positions (as described above), an audible indication will be created. Accordingly, the deflectable members 225a-b provide auditory and/or tactile feedback that the low-spillage quick disconnect 200 is arranged in the first configuration (which operatively allows for fluids to flow therethrough).

The first body portion 210 also includes a mechanism that engages with the core member 260 (FIGS. 40-43). For example, in the depicted embodiment the first body portion 210 includes a first projection 226a and a second projection 226b. The projections 226a-b function like a mechanical key member that engages with a corresponding recess 266 defined by the core member 260 (as described further below in reference to FIG. 42). The mechanical interaction between the projections 226a-b and the corresponding recess defined by the core member 260 serves to limit how much the core member 260 can rotate or pivot in relation to the first body portion 210.

In some embodiments, the first body portion 210 (and/or one or more other components of the low-spillage quick disconnect 200) is made of a thermoplastic material. In particular embodiments, the first body portion 210 is made of a thermoplastic, such as, but not limited to, polycarbonate, polysulfone, polyether ether ketone, polysulphide, polyester, polyvinylidene fluoride (PVDF), polyethylene, polyphenylsulfone (PPSU; e.g., Radel®), polyetherimide (PEI; e.g., Ultem®), polypropylene, polyphenylene, polyaryletherketone, Acrylonitrile butadiene styrene (ABS), and the like, and combinations thereof. In some embodiments, the first body portion 210 (or one or more portions thereof) is transparent or translucent so that internal components and/or fluids are visible. In some embodiments, the first body portion 210 (or one or more portions thereof) are overmolded with a second type of moldable material. In some embodiments, the low-spillage quick disconnect 200 is entirely metallic-free. That is, in some embodiments no metallic materials are included in the low-spillage quick disconnect 200. In some embodiments, one or more of the components of the low-spillage quick disconnect 200 (e.g., the first body portion 210, the second body portion 240, etc.) are made of metals such as, but not limited to, stainless steel, brass, aluminum, beryllium copper, and the like.

In some embodiments, the inner wall 221 (or portions thereof) that defines the internal space 220 is overmolded or coated with a softer material that seals against the second body portion 240 and/or the shut-off member 230 (which can each be made of harder materials). For example, one or more portions of the inner wall 221 (or the majority thereof, or the entirety thereof) can be overmolded with a softer seal material such as, but not limited to, silicone, fluoroelastomers (FKM), ethylene propylene diene monomer (EPDM), thermoplastic elastomers (TPE), bursa, buna-N, thermoplastic vulcanizates (TPV), and the like. In some such embodiments, such a softer seal material is overmolded as an annular band around the aperture 228. Alternatively, some embodiments of the first body portion 210 include an o-ring seal member positioned around the aperture 228.

It should be understood that the inclusion of features to create one or more such seals between the first body portion 210 and the second body portion 240 and/or the shut-off member 230 can serve to maintain the sterility of a sterilized low-spillage quick disconnect 200 during storage and use. That is, such seal(s) prevents the entrance of bio-contamination between the first body portion 210 and the second body portion 240 and/or shut-off member 230 that could otherwise enter into the first and second lumens defined by the first and second body portions 210 and 240. The seal performs that role during storage, and also during reconfiguration of the low-spillage quick disconnect 200 between the first and second coupled configurations (as shown in FIGS. 23 and 24).

While the seal(s) described above is/are comprised of a soft material on the surface of the inner wall 221 which abuts against a harder material of the second body portion 240 and/or the shut-off member 230, in some embodiments the locations of the soft and hard materials can be reversed. That is, in some embodiments the inner wall 221 of the first body portion 210 can be a hard material and one or more portions (or an entirety) of surface of the second body portion 240 and/or the shut-off member 230 can be overmolded with a softer material.

The first body portion 210 also defines a first aperture 228 that is at an opposite end of the fluid handling connection 211 that defines the first lumen extending from the first port 212. When the first body portion 210 is separated from the second body portion 240 (as shown in FIG. 25), the first aperture 228 is occluded so that fluid spillage from the first body portion 210 is inhibited and substantially prevented.

Referring also to FIGS. 32-35, the shut-off member 230 is movably positioned within, and remains captured within, the internal space 220 so that it can occlude the first aperture 228 while the first body portion 210 is separated from the second body portion 240 (as shown in FIG. 25). The first body portion 210 defines an annular seal seat 229 that slidably receives a correspondingly-sized and shaped seal base 232 of the shut-off member 230.

In the depicted embodiment, the first body portion 210 includes an undercut area 227 (FIG. 30) that engages with one or more tab members 235 positioned around the inner circumference of the annular seal base 232 to mechanically detain the shut-off member 230 in the first body portion 210 while allowing relative rotation of the shut-off member 230 in relation to the first body portion 210. Indeed, the shut-off member 230 and the first body portion 210 remain coupled together during use (both while the body portions 210 and 240 are coupled, and while the body portions 210 and 240 are separated). In some embodiments, the annular seal base 232 defines an optional split (e.g., the annular seal base 232 is an open C-shape) to facilitate assembly of the shut-off member 230 to the first body portion 210.

Extending from the annular seal base 232 is a sidewall portion 234. The sidewall portion 234 is sized and shaped to releasably engage with a correspondingly-sized and shaped cutout defined by the second body portion 240 (as described further below in reference to FIGS. 36-39).

The sidewall portion 234 includes a sealing projection 236. The sealing projection 236 is sized, shaped, and positioned to releasably engage with the first aperture 228 like a plug or a stopper. The sealing projection 236 is engaged with the first aperture 228 while the low-spillage quick disconnect 200 is configured in the second coupled configuration as shown in FIGS. 24 and 27, and while the first body portion 210 is separated from the second body portion 240 (as shown in FIG. 25). When the sealing projection 236 is engaged with the first aperture 228, a substantially fluid-tight seal is established (assuming an operating pressure that is consistent with the specifications of the particular low-spillage quick disconnect 200 being used).

The sidewall portion 234 also defines an aperture 238. The aperture 238 is sized shaped, and positioned to align with the first aperture 228 while the low-spillage quick disconnect 200 is configured in the first coupled configuration as shown in FIGS. 23 and 26. Accordingly, the aperture 238 defines a portion of the open flow path that exists between the first port 112 of the first body portion 110 and the second port 142 of the second body portion 140 while the low-spillage quick disconnect 200 is configured in the first coupled configuration.

While the depicted embodiment of the shut-off member 230 includes the sidewall portion 234 that is cantilevered from the annular seal base 232, alternative designs are also envisioned. For example, in some embodiments the sidewall portion 234 makes up a portion of a cylinder. That is, additional material is included such that, rather than having a cantilevered sidewall portion 234, the shut-off member 230 is shaped as a hollow cylinder and sidewall portion 234 is within or part of the wall of that hollow cylinder. Such a cylindrical design may provide advantages such as increased rigidity and shape-stability. In some such embodiments, the sidewall portion 234 can be thicker than other portions of the cylinder wall. That way the sidewall portion 234 can still mechanically engage with the second body portion 240 (as described further below). The optional split 233 can still be included in a cylindrical design. In such a case, the optional split 233 would be a notch out of the end of the cylinder.

The shut-off member 230 can be made of any of the materials described above in reference to the first body portion 210. Alternatively, or additionally, in some embodiments the shut-off member 230 (or portions thereof, e.g., by overmolding) is made of materials such as, but not limited to, silicone, FKM, bursa, buna-N, EPDM, TPE, TPV, and the like.

Referring to FIGS. 36-39, here an example second body portion 240 is shown in isolation from the other components of the low-spillage quick disconnect 200. Accordingly, greater detail of the second body portion 240 is now visible. The second body portion 240 can be made of any of the materials described above in reference to the first body portion 210.

Figure 28:
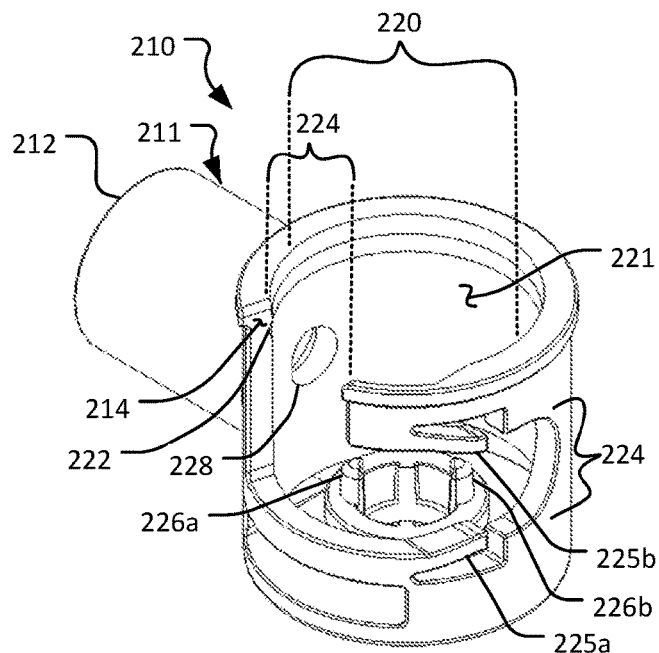
FIG. 28 is a perspective view of a first body portion of the low-spillage quick disconnect fluid coupling of FIG. 23.
Figure 31:
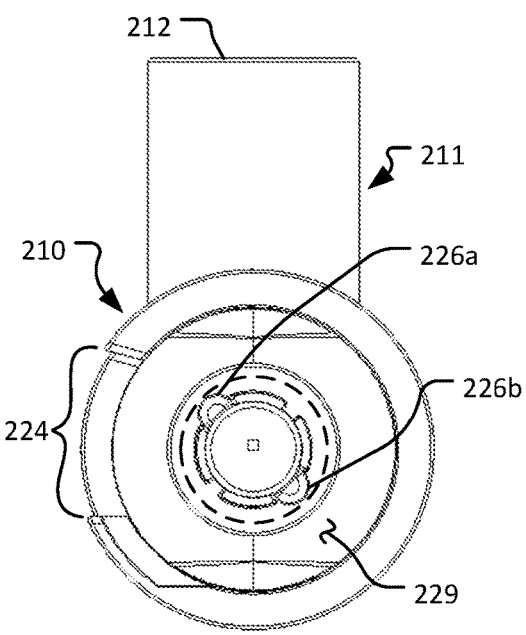
FIG. 31 is a top view of the first body portion of FIG. 28.
Figure 30:
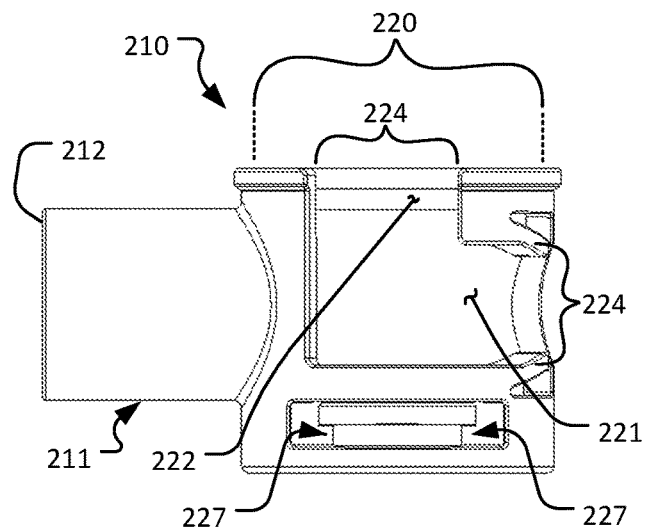
FIG. 30 is a side view of the first body portion of FIG. 28.
Figure 29:
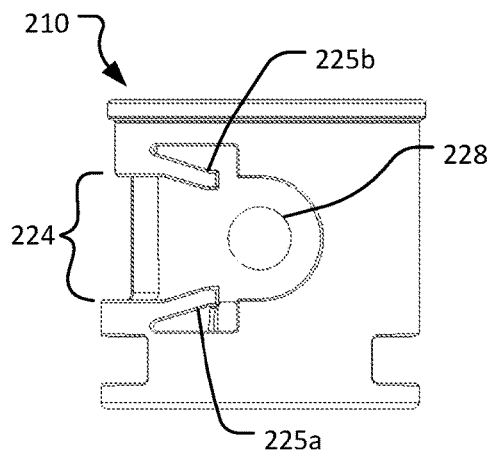
FIG. 29 is an end view of the first body portion of FIG. 28.
Figure 32:
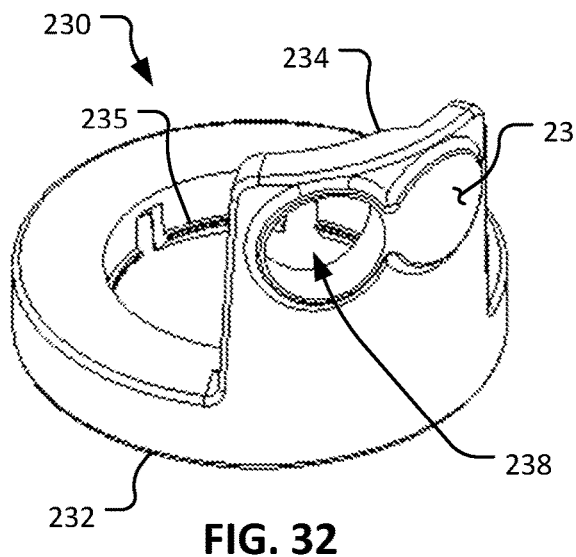
FIG. 32 is a perspective view of a shut-off member of the low-spillage quick disconnect fluid coupling of FIG. 23.
Figure 35:
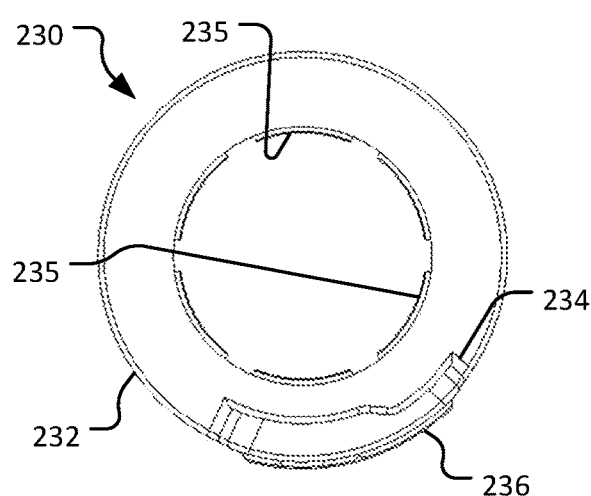
FIG. 35 is a top view of the shut-off member of FIG. 32.
Figure 34:
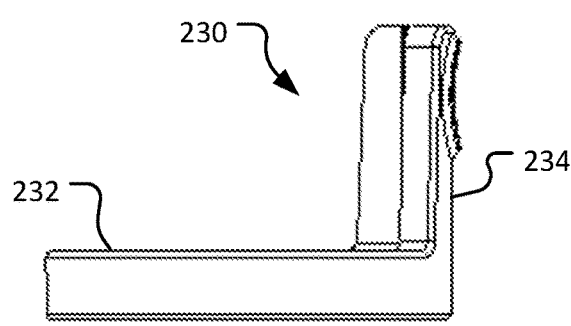
FIG. 34 is a side view of the shut-off member of FIG. 32.
Figure 33:
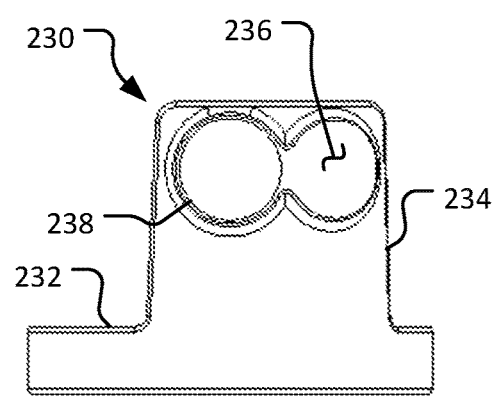
FIG. 33 is an end view of the shut-off member of FIG. 32.
Figure 41:
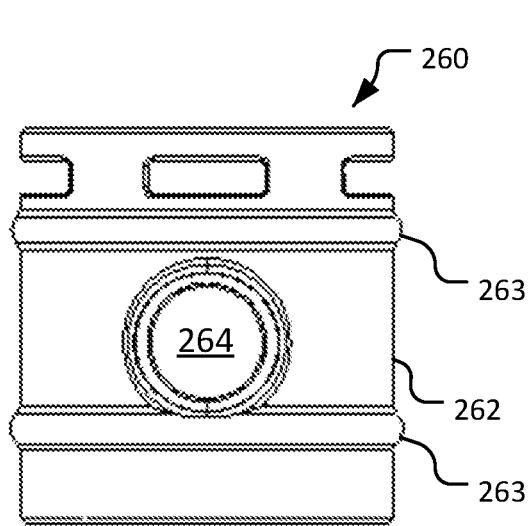
FIG. 41 is a side view of the core member of FIG. 40.
Figure 43:
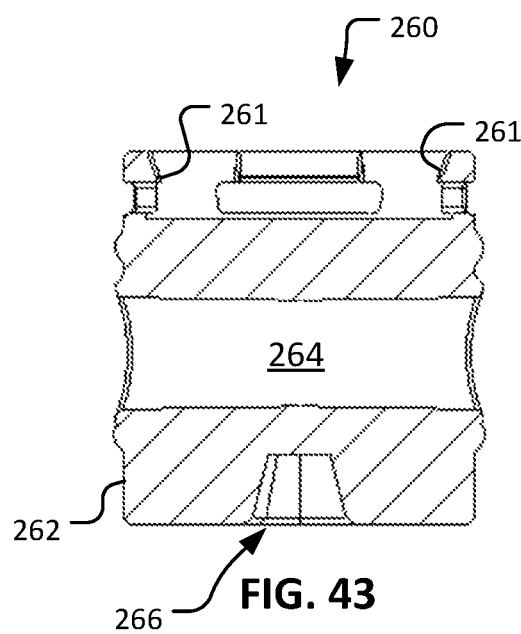
FIG. 43 is a cross-sectional view of the core member of FIG. 40.
Figure 42:
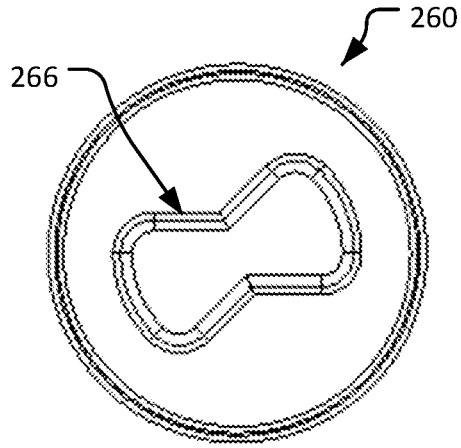
FIG. 42 is a bottom view of the core member of FIG. 40.
Figure 40:
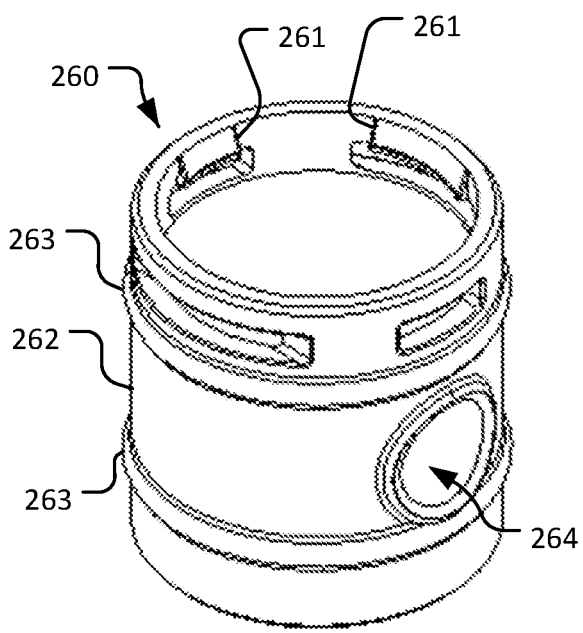
FIG. 40 is a perspective view of an example core member of the low-spillage quick disconnect fluid coupling of FIG. 23.
Figure 45:
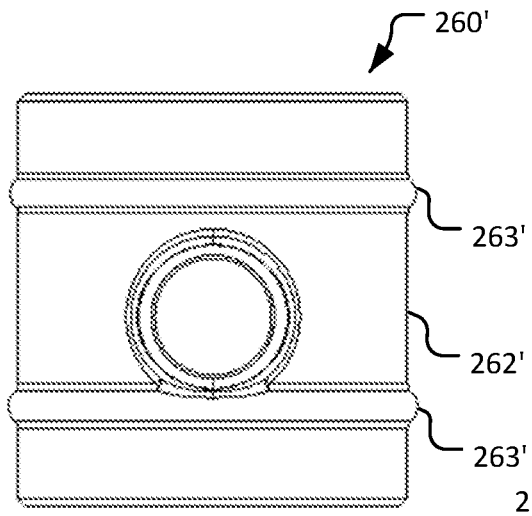
FIG. 45 is a side view of the core member of FIG. 44.
Figure 47:
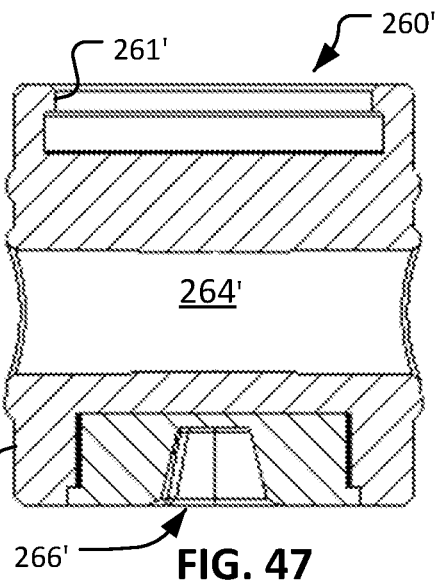
FIG. 47 is a cross-sectional view of the core member of FIG. 44.
Figure 46:
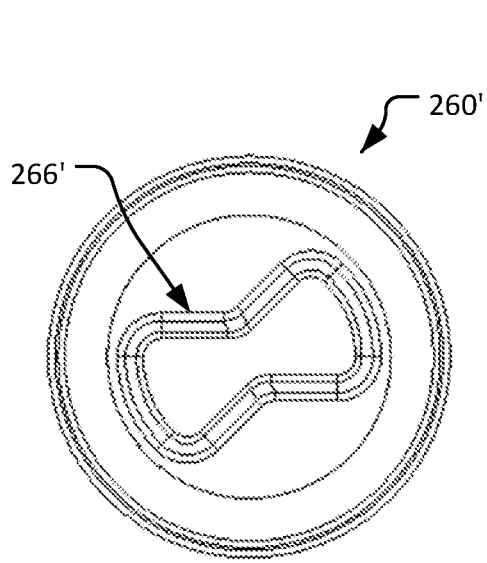
FIG. 46 is a bottom view of the core member of FIG. 44.
Figure 44:
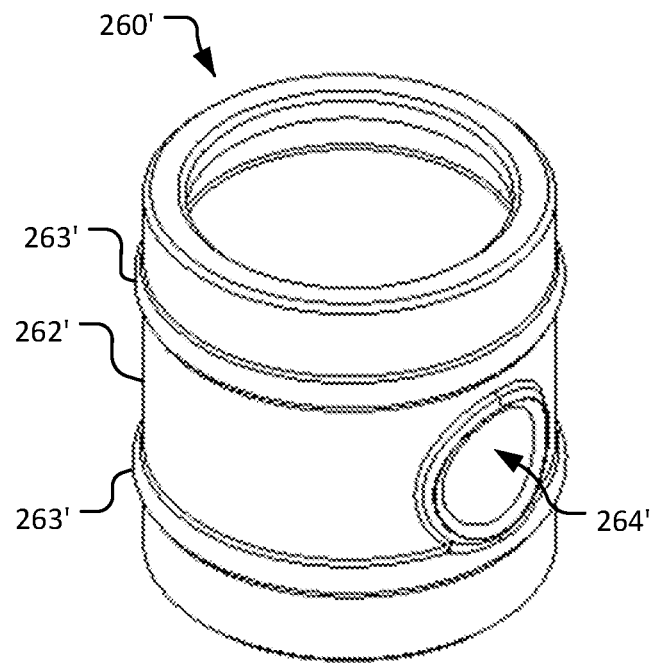
FIG. 44 is a perspective view of another example core member of the low-spillage quick disconnect fluid coupling of FIG. 23.

The second body portion 240 includes a generally cylindrical body 244 that is configured to be releasably received within the internal space 220 defined by the first body portion 210 as shown in FIGS. 28 and 30. The second body portion 240 also includes a fluid handling connection 241 that can extend through and travel within the L-shaped slot 224 of the first body portion 210.

Reference will now be made to the physical features of the second body portion 240 that were mentioned above as being releasably engageable with corresponding-sized and shaped features of the first body portion 210 or the shut-off member 230. For example, the second body portion 240 includes one or more protrusions 245 that is/are shaped and sized to releasably engage with, and slidingly mate with, the annular groove 222 of the first body portion 210 (FIGS. 28-31). Additionally, the second body portion 240 includes a cutout 246 that is sized and shaped to releasably engage with the sidewall portion 234 of the shut-off member 230 (FIGS. 32-35). The engagement between the cutout 246 and the sidewall portion 234 ensures that rotations of the second body portion 240 in relation to the first body portion 210 also cause corresponding rotations of the shut-off member 230 in relation to the first body portion 210. That physical relationship between the cutout 246 and the sidewall portion 234 is visible by comparing the configurations of FIGS. 26 and 27 to each other.

In the depicted embodiment, the cutout 246 is larger than the sidewall portion 234 of the shut-off member 230 (FIGS. 32-35). In other words, while the sidewall portion 234 of the shut-off member 230 is positioned within the cutout 246 of the second body portion 240, spatial clearance exists between the side(s) of the sidewall portion 234 and the cutout 246. Accordingly, while rotations of the second body portion 240 tend to drive rotations of the shut-off member 230 (as a result of the engagement between the cutout 246 and the sidewall portion 234), the resulting rotation of the shut-off member 230 will be less than the rotation of the second body portion 240 in some circumstances. For example, by comparing the configurations of FIGS. 26 and 27 to each other, it can be seen that while the second body portion 240 was rotated about 90 degrees the shut-off member 230 was rotated by about 30 degrees. The benefit of such an arrangement is that the exposure of the shut-off member 230 to the ambient environment is lessened. For example, as shown in FIG. 27, the shut-off member 230 is completely within the confines of the first body portion 210 while the low-spillage quick disconnect 200 is configured in the second coupled configuration. Additionally, as shown in FIG. 26, the shut-off member 230 is essentially completely within the confines of the first body portion 210 while the low-spillage quick disconnect 200 is configured in the first coupled configuration. Hence, especially while the low-spillage quick disconnect 200 is configured in the first coupled configuration, ambient contamination of the shut-off member 230 is advantageously prevented or inhibited because the cutout 246 of the second body portion 240 is larger than the sidewall portion 234 of the shut-off member 230.

While the depicted embodiment of the second body portion 240 includes the cutout 246, alternative designs are also envisioned. For example, in some embodiments the area of the cutout 246 can be a portion of the generally cylindrical body 244 with a thinner wall than other portions of the generally cylindrical body 244. Such a more completely cylindrical design of the second body portion 240 may provide advantages such as increased rigidity and shape-stability. Since the area of the cutout 246 would have a thinner wall than other portions of the generally cylindrical body 244, mechanical engagement between the second body portion 240 and the sidewall portion 234 of the shut-off member 230 would still be facilitated.

The generally cylindrical body 244 of the second body portion 240 also defines an aperture 247. The aperture 247 is at an opposite end of the fluid handling connection 241 that defines the second lumen extending from the second port 242. When the second body portion 240 is separated from the first body portion 210 (as shown in FIG. 25), the second aperture 247 is occluded by the core member 260 (as shown in FIG. 27) so that fluid spillage from the second body portion 240 is inhibited and substantially prevented.

The generally cylindrical body 244 of the second body portion 240 also defines an internal space 249. The internal space 249 is generally cylindrical. The cutout 246 and the aperture 247 are open to the internal space 249.

The depicted embodiment of the second body portion 240 also includes an annular undercut area 248 that mechanically engages (e.g., using a snap-in slip fit) with one or more tabs 261 of the core member 260 (refer to FIGS. 40 and 43), while still allowing for relative rotation between the second body portion 240 and the core member 260. Accordingly, the core member 260 and the second body portion 240 remain rotatably coupled together during use (during both: (i) while the body portions 210 and 240 are coupled, and (ii) while the body portions 210 and 240 are separated).

The second body portion 240 can also include a hard stop member 251 (FIG. 36). The hard stop member 251 is positioned to abut against a stop surface 214 (FIG. 28) of the first body portion 210 when the low-spillage quick disconnect 200 is configured in the second coupled configuration as shown in FIG. 24. That is, contact between the hard stop member 251 and the stop surface 214 establishes the rotational orientation between the first body portion 210 and the second body portion 240 while the low-spillage quick disconnect 200 is configured in the second coupled configuration.

Referring also to FIGS. 40-43, the core member 260 includes a generally cylindrical body 262 that can be movably positioned within internal space 249 of the second body portion 240 so that it can occlude the aperture 247 while the second body portion 240 is separated from the first body portion 210 (as shown in FIG. 25).

The core member 260 can be made of any of the materials described above in reference to the first body portion 210. Alternatively, or additionally, in some embodiments the core member 260 (or portions thereof, e.g., by overmolding) is made of materials such as, but not limited to, silicone, buna, buna-N, FKM, EPDM, TPE, TPV, and the like.

In some embodiments, the core member 260 can include one or more tabs 261. The one or more tabs 261 can be sized and shaped to releasably engage with, and slidingly mate with, a corresponding undercut area 248 (FIG. 38) that is defined within the internal space 249 of the second body portion 240. Engagement of the tabs 261 with such a corresponding undercut area 248 can ensure that the core member 260 remains coupled within the internal space 249 of the second body portion 240 while also being rotatably movable relative to the second body portion 240.

The core member 260 defines a lumen 264 that extends laterally, fully through the generally cylindrical body 262. In some embodiments, annular protrusions extending laterally from the generally cylindrical body 262 define the ends of the lumen 264. Such annular protrusions can help to seal the fluid flow path through the low-spillage quick disconnect 200 (while open and/or while closed).

Depending on the relative rotational position of the core member 260 in relation to the second body portion 260, the lumen 264 of the core member 260 can serve as a fluid flow path in conjunction with the aperture 247 of the second body portion 240 (and in conjunction with the aperture 238 of the shut-off member 230). That is, when the low-spillage quick disconnect 200 is in the first coupled configuration (FIGS. 23 and 26), an open fluid flow path is defined between the first and second ports 212 and 242. That open fluid flow path extends from the first port 212 through: (i) the lumen defined by the fluid handling connection 211 of the first body portion 210, (ii) the aperture 228 of the first body portion 210, (iii) the aperture 238 of the shut-off member 230, (iv) the lumen 264 of the core member 260, (v) the aperture 247 of the second body portion 240, (vi) the lumen defined by the fluid handling connection 241 of the second body portion 240, and then to the second port 242.

When the core member 260 is rotated in relation to the second body portion 240 such that the lumen 264 is not in alignment with the aperture 247, then the core member 260 occludes the aperture 247, and flow through the low-spillage quick disconnect 200 is prevented. Such an arrangement exists while the low-spillage quick disconnect 200 is in the second coupled configuration (FIGS. 24 and 27), and also while the first and second body portions 210 and 240 are separated from each other (FIG. 25). Moreover, while the lumen 264 is not in alignment with the aperture 247, then the lumen 264 is itself also occluded at each end thereof by the inner wall of the second body portion 240.

In the some embodiments, the core member 260 also includes one or more annular seals 263 partially or fully around the circumference of the core member 260. In the depicted embodiment, two annular seals 263 are included on opposite sides of the openings to the lumen 264. The one or more annular seals 263 can be made of a suitable type of compliant plastic or rubber.

The core member 260 also defines a recess 266. In the depicted embodiment, the recess 266 has a cross-sectional shape that resembles a bow tie. Like a mechanical key within a keyway, the recess 266 physically receives the projections 226a-b of the first body portion 210 (FIGS. 28-31), while defining additional clearance space there between. Since the recess 266 is larger than the projections 226a-b, the mechanical interaction between the projections 226a-b and the recess 266 allows the core member 260 to rotate or pivot in relation to the first body portion 210, but also limits how much the core member 260 can rotate or pivot in relation to the first body portion 210.

The recess 266 can be designed to allow any desired amount of relative rotation between the core member 260 and the first body portion 210. In the depicted embodiment, about 45 degrees of relative rotation is allowed by the mechanical interaction of the recess 266 and the projection 226. In some embodiments, an allowed relative rotation between the core member 260 and the first body portion 210 is within a range of about 40 degrees to about 50 degrees, or about 35 degrees to about 55 degrees, or about 30 degrees to about 60 degrees.

In some embodiments, the core member 260 is an injection molded part. In particular embodiments, a core member can be made using a two-shot (overmolded) process.

Referring to FIGS. 44-47, a core member 260' that is made using a two-shot (overmolded) process is depicted. The core member 260' includes a generally cylindrical body 262' that can be movably positioned within internal space 249 so that it can occlude the aperture 247 while the second body portion 240 is separated from the first body portion 210 (as shown in FIG. 25).

The core member 260' can be made of any of the materials described above in reference to the first body portion 210. Alternatively, or additionally, in some embodiments the core member 260' (or portions thereof, e.g., by overmolding) is made of materials such as, but not limited to, silicone, buna, buna-N, FKM, EPDM, TPE, TPV, and the like.

In some embodiments, the core member 260' can include one or more protrusions or tabs 261'. The one or more protrusions or tabs 261' can be sized and shaped to releasably engage with, and slidingly mate with, a corresponding undercut area 248 (FIG. 38) that is defined within the internal space 249 of the second body portion 240. Engagement of the one or more protrusions or tabs 261' within such a corresponding undercut area 248 can ensure that the core member 260' remains coupled within the internal space 249 of the second body portion 240 while also being rotatably movable relative to the second body portion 240.

The core member 260' defines a lumen 264' that extends laterally, fully through the generally cylindrical body 262'. In some embodiments, annular protrusions extending laterally from the generally cylindrical body 262' define the ends of the lumen 264'. Such annular protrusions can help to seal the fluid flow path through the low-spillage quick disconnect 200 (while open and/or while closed).

Depending on the relative rotational position of the core member 260' in relation to the second body portion 260', the lumen 264' of the core member 260' can serve as a fluid flow path in conjunction with the aperture 247 of the second body portion 240 (and in conjunction with the aperture 238 of the shut-off member 230). That is, when the low-spillage quick disconnect 200 is in the first coupled configuration (FIGS. 23 and 26), an open fluid flow path is defined between the first and second ports 212 and 242. That open fluid flow path extends from the first port 212 through: (i) the lumen defined by the fluid handling connection 211 of the first body portion 210, (ii) the aperture 228 of the first body portion 210, (iii) the aperture 238 of the shut-off member 230, (iv) the lumen 264' of the core member 260', (v) the aperture 247 of the second body portion 240, (vi) the lumen defined by the fluid handling connection 241 of the second body portion 240, and then to the second port 242.

When the core member 260' is rotated in relation to the second body portion 240 such that the lumen 264' is not in alignment with the aperture 247, then the core member 260' occludes the aperture 247, and flow through the low-spillage quick disconnect 200 is prevented. Such an arrangement exists while the low-spillage quick disconnect 200 is in the second coupled configuration (FIGS. 24 and 27), and also while the first and second body portions 210 and 240 are separated from each other (FIG. 25). Moreover, while the lumen 264' is not in alignment with the aperture 247, then the lumen 264' is itself also occluded at each end thereof by the inner wall of the second body portion 240.

In the some embodiments, the core member 260' also includes one or more annular seals 263' partially or fully around the circumference of the core member 260'. In the depicted embodiment, two annular seals 263' are included on opposite sides of the openings to the lumen 264'. The one or more annular seals 263' can be made of a suitable type of compliant plastic or rubber. The core member 260' also defines a recess 266'. In the depicted embodiment, the recess 266' has a cross-sectional shape that resembles a bow tie. Like a mechanical key within a keyway, the recess 266' physically receives the projections 226a-b of the first body portion 210 (FIGS. 28-31), while defining additional clearance space there between. Since the recess 266' is larger than the projections 226a-b, the mechanical interaction between the projections 226a-b and the recess 266' allows the core member 260' to rotate or pivot in relation to the first body portion 210, but also limits how much the core member 260' can rotate or pivot in relation to the first body portion 210.

The recess 266' can be designed to allow any desired amount of relative rotation between the core member 260' and the first body portion 210. In the depicted embodiment, about 45 degrees of relative rotation is allowed by the mechanical interaction of the recess 266' and the projection 226. In some embodiments, an allowed relative rotation between the core member 260' and the first body portion 210 is within a range of about 40 degrees to about 50 degrees, or about 35 degrees to about 55 degrees, or about 30 degrees to about 60 degrees.

Figure 48:
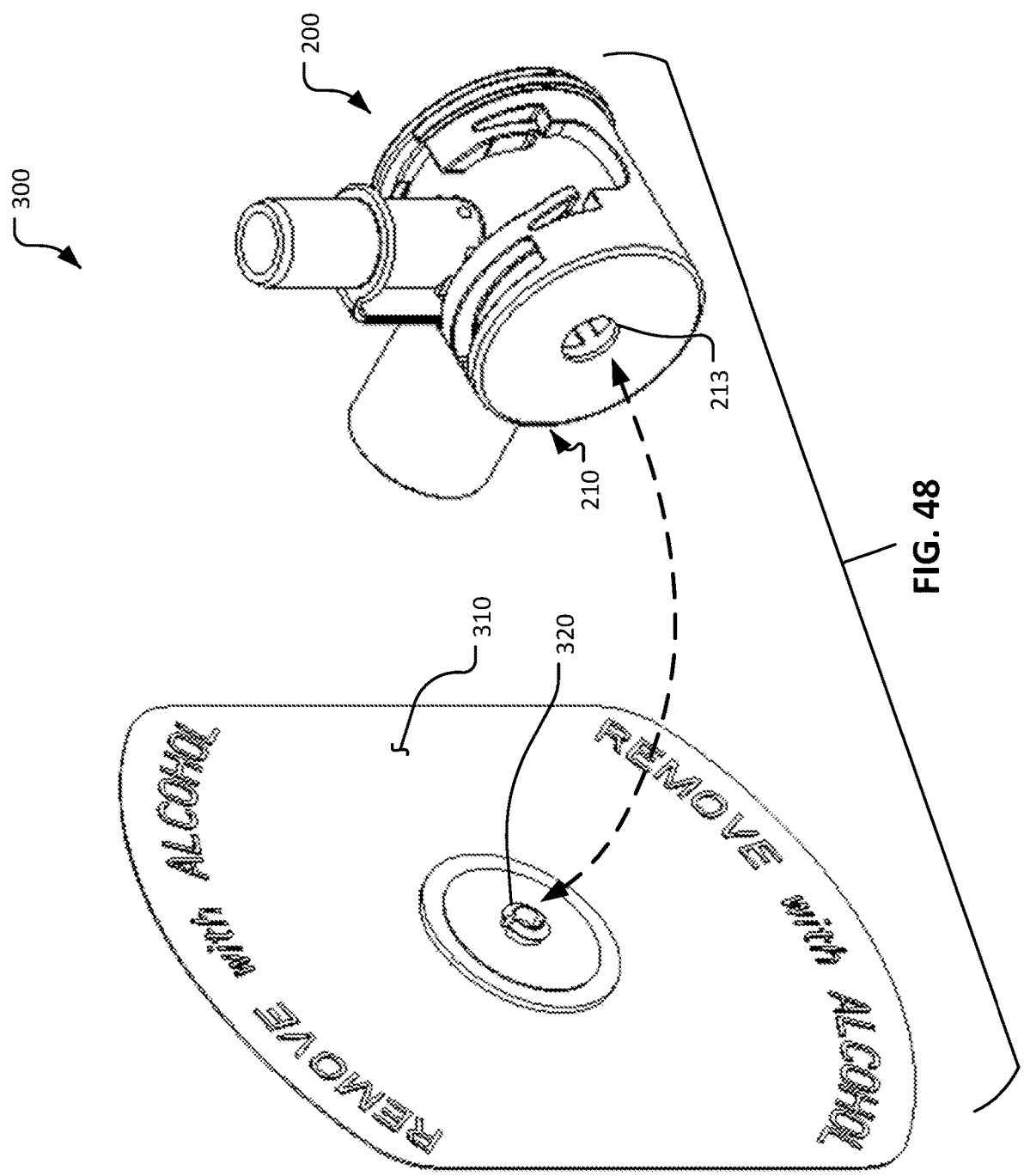
FIG. 48 is an exploded perspective view of a system for using the low-spillage quick disconnect fluid couplings described herein.
Figure 50:
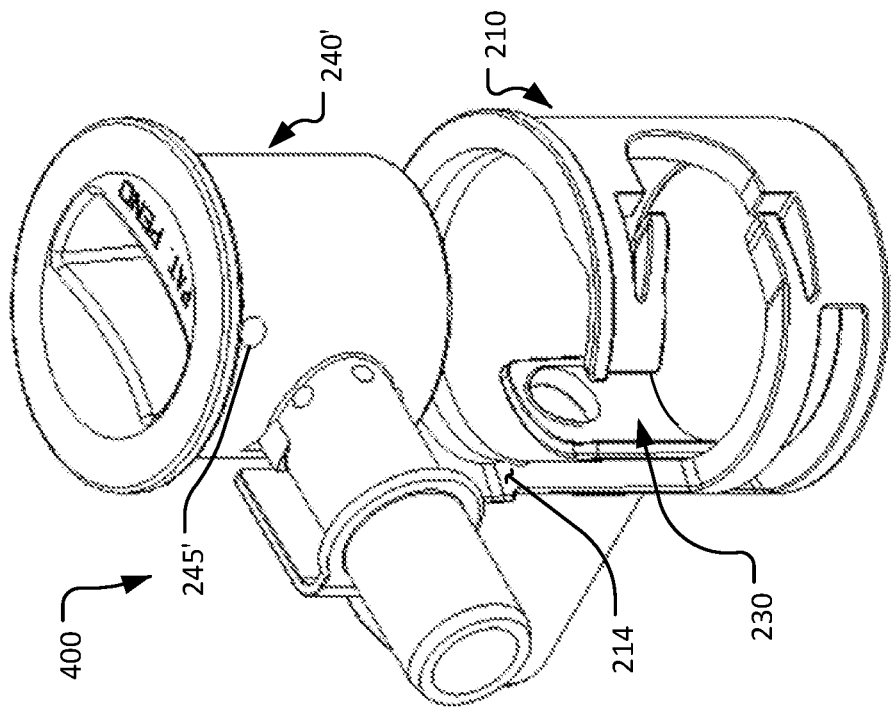
FIG. 50 is a perspective view of the low-spillage quick disconnect fluid coupling of FIG. 49. The low-spillage quick disconnect fluid coupling, as shown, is arranged in an uncoupled configuration.

Referring to FIG. 48, a system 300 includes the low-spillage quick disconnect 200 (or any other embodiment of low-spillage quick disconnect described herein) and a mounting patch 310. In some embodiments, the mounting patch 310 is an adhesive patch such that the mounting patch 310 can be adhered to surfaces such as, but not limited, a patient's skin or clothing.

The first body portion 210 of the low-spillage quick disconnect 200 can define an attachment feature 213. In the depicted embodiment, the attachment feature 213 is a recess. Other types of attachment features 213 are also envisioned such as, but not limited to, protrusions, threaded members, clips, and the like. The attachment feature 213 can be designed to releasably couple with a corresponding attachment feature 320 located on the mounting patch 310. In the depicted embodiment the attachment feature 320 is a protrusion that can snap into a releasably detained relationship with the attachment feature 213 of the low-spillage quick disconnect 200. In that fashion, the system 300 can allow the low-spillage quick disconnect 200 to be releasably affixed in a location relative to a patient while the low-spillage quick disconnect 200 is in use by the patient.

Referring to FIGS. 49-57, a low-spillage quick disconnect 400 that uses another type of second body portion 240' is shown. The second body portion 240' can be used with the first body portion 210 (e.g., FIGS. 28-31) and the shut-off member 230 (e.g., FIGS. 32-35) to create the low-spillage quick disconnect 400. In some embodiments, the low-spillage quick disconnect 400 can include the latch mechanism 270.

The low-spillage quick disconnect 400 does not need a core member (such as core member 160 or core member 260). In other words, the low-spillage quick disconnect 400 can include merely three parts: (i) the first body portion 210, (ii) the shut-off member 230, and (iii) the second body portion 240'. In result, though the shut-off member 230 seals the lumen defined by the fluid handling connection 211 of the first body portion 210 while the low-spillage quick disconnect 400 is configured in the second coupled configuration (FIGS. 49 and 56) and the uncoupled configuration (FIG. 50), a lumen 243' defined by the second body portion 240' is not sealed.

In FIGS. 51-54, the second body portion 240' is shown in isolation from the other components of the low-spillage quick disconnect 400. Accordingly, greater detail of the second body portion 240' is now visible. The second body portion 240' can be made of any of the materials described above in reference to the first body portion 210.

The second body portion 240' includes a generally cylindrical body 244' that is configured to be releasably received within the internal space 220 defined by the first body portion 210 as shown in FIGS. 28 and 30. The second body portion 240' also includes a fluid handling connection 241' that can extend through and travel within the L-shaped slot 224 of the first body portion 210.

Reference will now be made to the physical features of the second body portion 240' that can be releasably engageable with corresponding-sized and shaped features of the first body portion 210 or the shut-off member 230. For example, the second body portion 240' includes one or more protrusions 245' that is/are shaped and sized to releasably engage with, and slidingly mate with, corresponding features of the first body portion 210 (e.g., the annular groove 222 as shown in FIGS. 28-31). Additionally, the second body portion 240' includes a cutout 246' that is sized and shaped to releasably engage with the sidewall portion 234 of the shut-off member 230 (FIGS. 32-35). The engagement between the cutout 246' and the sidewall portion 234 ensures that rotations of the second body portion 240' in relation to the first body portion 210 also cause rotations of the shut-off member 230 in relation to the first body portion 210. That physical relationship between the cutout 246' and the sidewall portion 234 is visible by comparing the configurations of FIGS. 55 and 56 to each other.

Figure 49:
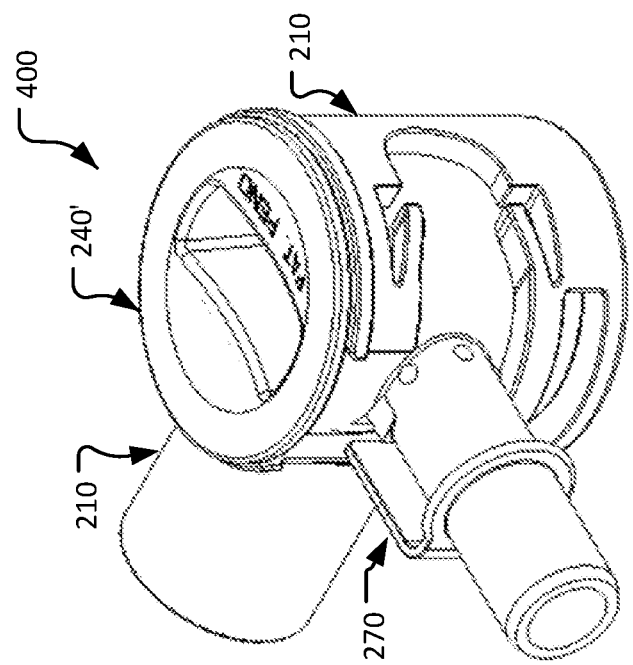
FIG. 49 is a perspective view of another example low-spillage quick disconnect fluid coupling in accordance with some embodiments. The low-spillage quick disconnect fluid coupling, as shown, is arranged in a coupled configuration that closes a flow path through the low-spillage quick disconnect fluid coupling.

The second body portion 240' can also include a hard stop member 251' (FIG. 54). The hard stop member 251' is positioned to abut against a stop surface 214 (FIG. 28) of the first body portion 210 when the low-spillage quick disconnect 400 is configured in the second coupled configuration as shown in FIG. 49. That is, as depicted in the cross-sectional view of FIG. 57, contact between the hard stop member 251' and the stop surface 214 establishes the rotational orientation between the first body portion 210 and the second body portion 240' while the low-spillage quick disconnect 400 is configured in the second coupled configuration.

In the depicted embodiment, the cutout 246' is larger than the sidewall portion 234 of the shut-off member 230 (FIGS. 32-35). In other words, while the sidewall portion 234 of the shut-off member 230 is positioned within the cutout 246' of the second body portion 240', spatial clearance exists between the side(s) of the sidewall portion 234 and the cutout 246'. Accordingly, while rotations of the second body portion 240' tend to drive rotations of the shut-off member 230 (as a result of the engagement between the cutout 246' and the sidewall portion 234), the resulting rotation of the shut-off member 230 will be less than the rotation of the second body portion 240' in some circumstances. For example, by comparing the configurations of FIGS. 55 and 56 to each other, it can be seen that while the second body portion 240' was rotated about 90 degrees the shut-off member 230 was rotated by about 30 degrees. The benefit of such an arrangement is that the exposure of the shut-off member 230 to the ambient environment is lessened. For example, as shown in FIG. 56, the shut-off member 230 is completely within the confines of the first body portion 210 while the low-spillage quick disconnect 400 is configured in the second coupled configuration. Additionally, as shown in FIG. 55, the shut-off member 230 is essentially completely within the confines of the first body portion 210 while the low-spillage quick disconnect 400 is configured in the first coupled configuration. Hence, especially while the low-spillage quick disconnect 400 is configured in the first coupled configuration, ambient contamination of the shut-off member 230 is advantageously prevented or inhibited because the cutout 246' of the second body portion 240' is larger than the sidewall portion 234 of the shut-off member 230.

While the depicted embodiment of the second body portion 240' includes the cutout 246', alternative designs are also envisioned. For example, in the depicted embodiment the area of the cutout 246' includes a portion of the generally cylindrical body 244' that has a thinner wall than other portions of the generally cylindrical body 244'. Such a more partially complete cylindrical design of the second body portion 240' may provide advantages such as increased rigidity and shape-stability. Since the area of the cutout 246' that has a thinner wall than other portions of the generally cylindrical body 244' still allows for mechanical engagement between the second body portion 240' and the sidewall portion 234 of the shut-off member 230 (as seen in FIGS. 55 and 56).

The lumen 243' extends from the second port 242' of the fluid handling connection 241' to an aperture 247'. Accordingly, while the low-spillage quick disconnect 400 is configured in the first coupled configuration (FIG. 55) an open flow path extends from the first port 212 through: (i) the lumen defined by the fluid handling connection 211 of the first body portion 210, (ii) the aperture 228 of the first body portion 210, (iii) the aperture 238 of the shut-off member 230, (iv) the aperture 247' of the second body portion 240', and (v) the lumen 243' defined by the second body portion 240', and then to the second port 242'.

Optional Additional Features:

In some embodiments, an additional feature or component is included to prevent accidental or inadvertent reconfiguration of the low-spillage quick disconnect 100 away from the first coupled configuration in which an open flow path exists between the first port 112 of the first body portion 110 and the second port 142 of the second body portion 140. For example, in some embodiments a latch mechanism is included that must be actuated to allow relative rotation of the first and second body portions 110 and 140. In some embodiments, a cover component is included that retains the first and second body portions 110 and 140 in the first coupled configuration (in which the fluid handling connections 111 and 141 are linearly aligned). In some cases, such a cover component must be removed to allow relative rotation of the first and second body portions 110 and 140. In some cases, such a cover component can be integral to the low-spillage quick disconnect 100 so that it can be pivoted, deflected, slid, or otherwise moved out of the way to allow relative rotation of the first and second body portions 110 and 140 while not totally separating the cover component from other portions of the low-spillage quick disconnect 100.

In some embodiments, the fluid handling connections of the body portions described herein can include a flange or physical stop member that positionally limits the installation depth of a tube that is pressed onto the fluid handling connections. Excessive tube installation could cause interference with the rotational action of the low-spillage quick disconnects and flanges or stop members can prevent such a situation.

In some implementations, the assembled the low-spillage quick disconnects described herein (and, potentially, other fluid handling components connected thereto) is sterilized prior to use. Any suitable sterilization method can be used, such as gamma sterilization, ethylene oxide sterilization, e-beam sterilization, Noxilizer™ sterilization, Revox® sterilization, or using an autoclave, and the like. In some cases, the assembled the low-spillage quick disconnect may be coupled with tubing and/or other components prior to sterilization, and the assembly is sterilized in the coupled/assembled configuration.

While this specification contains many specific implementation details, these should not be construed as limitations on the scope of any invention or of what may be claimed, but rather as descriptions of features that may be specific to particular embodiments of particular inventions. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described herein as acting in certain combinations and even initially claimed as such, one or more features from a claimed combination can in some cases be excised from the combination, and the claimed combination may be directed to a subcombination or variation of a subcombination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system modules and components in the embodiments described herein should not be understood as requiring such separation in all embodiments, and it should be understood that the described program components and systems can generally be integrated together in a single product or packaged into multiple products.

Particular embodiments of the subject matter have been described. Other embodiments are within the scope of the following claims. For example, the actions recited in the claims can be performed in a different order and still achieve desirable results. As one example, the processes depicted in the accompanying figures do not necessarily require the particular order shown, or sequential order, to achieve desirable results. In certain implementations, multitasking and parallel processing may be advantageous.

What is claimed is:

1. A fluid handling device, comprising:
   a first body portion defining a first lumen extending between a first port and a first aperture along a first axis;
   a second body portion defining a second lumen extending between a second port and a second aperture along a second axis; and
   a core member pivotably coupled with the second body portion,
   wherein the first and second body portions are: (i) coupleable with each other and (ii) separable from each other,
   wherein, while the first and second body portions are separated from each other, the first and second apertures are each occluded,
   wherein, while the first and second body portions are coupled with each other, the fluid handling device is configurable in: (a) a first coupled configuration in which an open flow path is defined between the first and second ports and (b) a second coupled configuration in which the first and second apertures are each occluded, and
   wherein the first and second body portions are pivotable in relation to each other about a central axis that is transverse to each of the first and second axes in order to reconfigure the fluid handling device between the first and second coupled configurations and to cause the core member to pivot in relation to each of the first and second body portions.

2. The fluid handling device of claim 1, wherein an engagement mechanism between the first body portion and the core member limits how much the core member can pivot in relation to the first body portion.

3. The fluid handling device of claim 1, wherein the core member defines a central lumen, and wherein the open flow path comprises the central lumen.

4. The fluid handling device of claim 3, wherein the open flow path is linear and unobstructed.

5. The fluid handling device of claim 3 wherein, while the first and second body portions are separated from each other, each end of the central lumen is occluded by the second body portion.

6. The fluid handling device of claim 1, wherein, while the first and second body portions are separated from each other, the first aperture is directly occluded by a shut off member that includes a sealing projection that releasably engages with the first aperture to establish a substantially fluid-tight seal there between.

7. The fluid handling device of claim 1, wherein, while the first and second body portions are separated from each other, the second aperture is directly occluded by the core member.

8. The fluid handling device of claim 7, wherein the second body portion further defines a third aperture.

9. The fluid handling device of claim 8, wherein the third aperture forms a portion of the open flow path.

10. The fluid handling device of claim 9, wherein while the first and second body portions are separated from each other, the third aperture is directly occluded by the core member.

11. The fluid handling device of claim 1, wherein the first and second body portions are separable from each other by moving them along the central axis away from each other.

12. A fluid handling device, comprising:
   a first body portion defining a first lumen extending between a first port and a first aperture along a first axis;
   a second body portion defining: (i) a second port, (ii) a second aperture, (iii) a second lumen extending along a second axis between the second port and the second aperture, and (ii) a third aperture; and
   a core member movably coupled with the second body portion, wherein the core member defines a central lumen,
   wherein the first and second body portions are: (i) coupleable with each other and (ii) separable from each other,
   wherein, while the first and second body portions are separated from each other, the first and second apertures are each occluded,
   wherein, while the first and second body portions are coupled with each other, the fluid handling device is configurable in: (a) a first coupled configuration in which an open flow path is defined between the first and second ports and (b) a second coupled configuration in which the first and second apertures are each occluded,
   wherein the open flow path comprises the central lumen defined by the core member,
   wherein the first and second body portions are pivotable in relation to each other about a central axis that is transverse to each of the first and second axes in order to reconfigure the fluid handling device between the first and second coupled configurations, and
   wherein, while the first and second body portions are separated from each other, the second aperture is directly occluded by the core member.

13. The fluid handling device of claim 12, wherein the first and second body portions are separable from each other by moving them along the central axis away from each other.

14. The fluid handling device of claim 12, wherein the open flow path is linear and unobstructed.

15. The fluid handling device of claim 12, wherein, while the first and second body portions are separated from each other, each end of the central lumen is occluded by the second body portion.

16. A fluid handling device, comprising:
- a first body portion defining a first lumen extending between a first port and a first aperture along a first axis; and
- a second body portion defining a second lumen extending between a second port and a second aperture along a second axis,
- wherein the first and second body portions are: (i) coupleable with each other and (ii) separable from each other,
- wherein, while the first and second body portions are separated from each other, the first and second apertures are each occluded,
- wherein, while the first and second body portions are coupled with each other, the fluid handling device is configurable in: (a) a first coupled configuration in which an open flow path is defined between the first and second ports and (b) a second coupled configuration in which the first and second apertures are each occluded,
- wherein the first and second body portions are pivotable in relation to each other about a central axis that is transverse to each of the first and second axes in order to reconfigure the fluid handling device between the first and second coupled configurations, and
- wherein the first and second body portions are separable from each other by moving them along the central axis away from each other.

17. The fluid handling device of claim 16, further comprising a core member movably coupled with the second body portion, wherein the core member defines a central lumen, and wherein the open flow path comprises the central lumen.

18. The fluid handling device of claim 17, wherein the open flow path is linear and unobstructed.

19. The fluid handling device of claim 17, wherein, while the first and second body portions are separated from each other, each end of the central lumen is occluded by the second body portion.

20. The fluid handling device of claim 17, wherein, the second body portion further defines a third aperture, wherein the third aperture forms a portion of the open flow path, and wherein while the first and second body portions are separated from each other, the third aperture is directly occluded by the core member.

* * * * *

UNITED STATES PATENT AND TRADEMARK OFFICE
CERTIFICATE OF CORRECTION

| | |
|---|---|
| PATENT NO. | : 11,612,731 B2 |
| APPLICATION NO. | : 16/645074 |
| DATED | : March 28, 2023 |
| INVENTOR(S) | : Elizabeth J. Langer, Randall S. Williams and Gary J. Harris |

It is certified that error appears in the above-identified patent and that said Letters Patent is hereby corrected as shown below:

On the Title Page

Column 1 (Item (87) PCT Pub. No.), Line 1: Delete "WO2019/167891" and insert -- WO2019/067891 --.

In the Claims

Column 28, Line 8: In Claim 5, delete "claim 3" and insert -- claim 3, --.

Column 28, Line 25: In Claim 10, delete "wherein" and insert -- wherein, --.

Column 30, Line 18: In Claim 20, delete "wherein," and insert -- wherein --.

Column 30, Line 21: In Claim 20, delete "wherein" and insert -- wherein, --.

Signed and Sealed this
Twenty-second Day of August, 2023

Katherine Kelly Vidal
*Director of the United States Patent and Trademark Office*